United States Patent
Tsai et al.

(10) Patent No.: US 8,680,142 B2
(45) Date of Patent: Mar. 25, 2014

(54) ASCORBATE, VITAMIN K3 AND HYDROXYTOLANS IN THE TREATMENT OF CANCER

(75) Inventors: Chun-che Tsai, Kent, OH (US); James M. Jamison, Stow, OH (US); Jackie L. Summers, Sun City Center, FL (US)

(73) Assignees: Kent State University, Kent, OH (US); Summa Health System, Akron, OH (US)

( * ) Notice: Subject to any disclaimer, the term of this patent is extended or adjusted under 35 U.S.C. 154(b) by 562 days.

(21) Appl. No.: 12/666,080

(22) PCT Filed: Jun. 20, 2008

(86) PCT No.: PCT/US2008/067602
§ 371 (c)(1),
(2), (4) Date: Mar. 18, 2011

(87) PCT Pub. No.: WO2008/157745
PCT Pub. Date: Dec. 24, 2008

(65) Prior Publication Data
US 2011/0160301 A1    Jun. 30, 2011

Related U.S. Application Data

(60) Provisional application No. 60/945,263, filed on Jun. 20, 2007.

(51) Int. Cl.
*A01N 43/08* (2006.01)
*A61K 31/34* (2006.01)

(52) U.S. Cl.
USPC ........................................................ 514/474

(58) Field of Classification Search
None
See application file for complete search history.

(56) References Cited

U.S. PATENT DOCUMENTS

| 5,556,871 | A  | 9/1996  | Halperin |
| 2003/0073738 | A1 | 4/2003  | Gilloteaux |
| 2003/0203974 | A1 | 10/2003 | Docherty |
| 2005/0267175 | A1 | 12/2005 | Shaw |

OTHER PUBLICATIONS

Fidler (Cancer Res 1978;38:2651-2660).*
Neidle, Stephen, ed. (Cancer Drug Design and Discovery, Publisher: Elsevier/Academic Press, 2008) pp. 427-431.*

* cited by examiner

*Primary Examiner* — James D Anderson
*Assistant Examiner* — William Lee
(74) *Attorney, Agent, or Firm* — Browdy and Neimark, PLLC

(57) ABSTRACT

The combination of compounds of the hydroxytolan family with ascorbate plus naphthoquinone (Vitamin K3; VK3), or a quinone or semiquinone analogue of VK3, kill tumor cells, inhibit tumor growth and development, and treat cancer in subjects in need thereof.

26 Claims, No Drawings

ASCORBATE, VITAMIN K3 AND HYDROXYTOLANS IN THE TREATMENT OF CANCER

FIELD OF THE INVENTION

The invention in the field of biochemistry and medicine relates to combination therapy of cancer using compounds of the hydroxytolan (HT) family in combination with ascorbate and naphthoquinone (Vitamin $K_3$ or "$VK_3$") or a quinone or semiquinone analogue of $VK_3$.

DESCRIPTION OF THE BACKGROUND ART

It is believed that 554,740 Americans died from cancer in 1996. Ten years later, the National Cancer Institute estimated that 570,280 Americans would die of cancer annually. Existing cancer treatment technologies are clearly not sufficient. Despite notable progress, there is a continuing need for better drugs and therapeutic modalities to combat cancer and improve the quality and the duration of life of cancer patients. Of particular interest are orally active agents that possesses antitumor activity either alone or in conjunction with other chemotherapeutic or anticancer agents.

The role of vitamins in cancer prevention and treatment has been a subject of interest. Ascorbate is known to act as an adjunct in improving responses to various types of cancer therapies by potentiating growth inhibitory effects of certain agents and increasing the cytotoxicity of others. Ascorbate may even reverse malignant cell transformation. The combination of Vitamin C and Vitamin $K_3$ has been studied as a possible potentiating therapeutic modality for conventional chemotherapy. See, for example, U.S. Pat. No. 7,091,241 (by several of the present inventors and colleagues; Taper H S et al., 1987, *Int J Cancer.* 40:575-9; Noto V et al., *Cancer* 1989, 63:901-6; Taper H S et al., *Anticancer Res.* 1992, 12:1651-4; De Loecker W et al., *Anticancer Res.* 1993, 13:103-6; Taper H S et al., 1996, *Anticancer Res.* 16:499-503). The present inventors have now discovered that the active tolan compounds of the present invention combined with ascorbate are useful for inhibiting cancer cell proliferation, inhibiting tumor angiogenesis, promoting tumor cell apoptosis, and thereby treating subjects with cancer.

Vitamin C/Ascorbate

The chemical structure of Vitamin C (sodium ascorbate) is shown below:

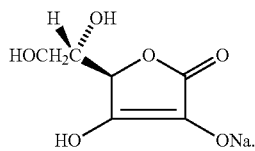

Vitamin C (abbreviated herein as "VitC or "VC") acts as a pro-oxidant, and has been evaluated as an antitumor agent. Several in vitro studies demonstrated that VC selectively accumulated in, and was toxic to, a variety of human tumor cells in culture. These included malignant melanoma cells, leukemia cells, neuroblastoma cells, ascites tumor cells as well as acute lymphoblastic leukemia, epidermoid carcinoma and fibrosarcoma cells.

Several case reports describe favorable outcomes in cancer patients undergoing high dose intravenous VC therapy. E. Cameron and L. Pauling (*Proc Natl Acad Sci USA* 73:3685-9, 1976). reported the effect of administering supplemental ascorbate (10 g/day intravenously (i.v.) for 10 days followed by 10 g/day orally thereafter) to 100 terminal cancer patients as part of routine management of these patients. The "controls," 1000 subjects matched for age and sex, were left untreated. These were individuals who suffered from cancer of the same primary organ type and histological type as the patient group. The mean survival time (MST) for ascorbate-treated subjects (>210 days) was more than 4.2 times greater than that of the controls (50 days) (p<<0.0001). Six of the 100 treated subjects had ovarian cancer. When their progress was compared to that of disease-matched controls, the MST of 148 days was twice as long as the controls (MST: 71 days; p<0.005). The results suggested that VC may be of value in the treatment of advanced ovarian cancer. Two later randomized, double-blind, placebo-controlled, clinical trials (Creagen et al., *New Eng. J. Med.* 301:687-690, 1979; Moertel et al., *New Eng. J. Med.* 312:137-141, 1985) that were designed to evaluate the effectiveness of 10 g of oral VC in patients with advanced cancer, reported no benefits of oral VC treatment. More recently, these studies have been criticized (Riordan et al., *Med. Hypotheses* 44:207-213, 1995) because the oral VC dose of 10 g/day is not believed to be sufficient to achieve plasma concentrations that were found to be cytotoxic for tumor cells in culture. Finally, a number of case studies (Riordan et al., supra; Riordan et al., *P.R. Health Sci. J.* 23:115-118, 2004; Drisko et al., *J. Am. Coll. Nutr.* 22:118-23, 2003) reported the effects of high i.v. doses of VC in patients with breast, colorectal, ovarian, pancreatic, renal cell carcinoma. VC doses ranged from 10 to 100 g given twice per week with the majority of doses being 60-70 g per infusion. The results of these case reports suggested that high i.v. doses of VC do not interfere with conventional anticancer therapy; are generally not toxic to cancer patients with normal renal function; and induce a small number of complete remissions. This high dose i.v. regimen of VC administration, while manifesting antitumor activity, is financially burdened an inconvenient as it requires additional doctor visits.

VC usage in humans is well-documented, and the vitamin is well tolerated in animals. Mice given daily VC doses of 6.5 g/Kg body weight for 6 weeks and 2 g/Kg for 2 years showed no abnormal rates of mortality, weight changes, blood chemistry, hematology, histology, or other pathologies (Klenner, F R, 1951, *South Med J* 113:101-7). This reference includes a table of therapeutic doses ranging from 35 g/day for a 220 pound man to 1.2 g/day in infants. Also indicated were maintenance doses of 60 mg/kg/day (i.e., about 2180 mg/day) and 75 mg/day for these respective groups. The only systemic toxicity noted at these doses has been diarrhea/gastrointestinal upset, in which case the doses are injected, bypassing these complications.

Vitamin $K_3$/Naphthoquinone

Vitamin $K_3$ ("$VK_3$; or menadione is a polycyclic aromatic ketone, based on 1,4-naphthoquinone, with a 2-methyl substituent. Its chemical name is 2-methyl-1,4-naphthoquinone or 2-methylnaphthalene-1,4-dione, and its the chemical formula is $C_{11}H_8O_2$, molecular mass 172.18. The chemical structure is shown below.

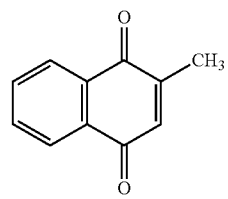

This synthetic derivative of vitamin $K_1$ exhibits antitumor activity against tumor cell lines from liver, cervix, nasopharynx, colon, lung, stomach, breast, leukemia and lymphoma (Nutter et al., *Biochem. Pharmacol.* 41:1283-92, 1991; Wu et al., *Life Sci.* 52:1797-804, 1993; Wu et al., *Br. J. Cancer* 35:1388-1393, 1999). Vitamin $K_3$ and its derivatives have also been employed as radiosensitizers because of their ability to concentrate selectively in malignant cells of various human tumors and metastases (including liver, kidney, bladder, prostate, stomach, intestine and colon cancers) while minimally accumulating in bone marrow (Halsall et al., *Urology* 1:550-2, 1973; Marrian et al., *Acta radiol. Ther. Phys. Biol.* 8:221-46, 1969). $VK_3$ has also proven effective against multiple drug-resistant leukemia cell lines and adriamycin-resistant leukemia cells in rats (Nutter et al., supra; Parekh et al., *Cancer Lett.* 61:147-56, 1992). Weekly i.p. administration of $VK_3$ (10 mg/2 mL) to hepatoma-bearing rats for 4 weeks increased survival to 60 days for test rats compared to 17 days for controls and resulted in 5 out of 16 long term survivors (Su et al., *Gaoxiong Yi Xue Ke Xue Za Zhi* 7:454-9, 1991). $VK_3$ (150-200 mg/day i.v.) has been shown (Mitchell et al., *Acta Radiol. Ther. Phys. Biol* 3:329-41, 1965) to radiosensitize patients with inoperable bronchial carcinoma and to chemosensitize patients to chemotherapeutic agents. When $VK_3$ was added to cultured human oral epidermoid carcinoma cells with another chemotherapeutic agent, synergism was observed with bleomycin, cisplatin, dicarbazine and 5-fluorouracil (5-FU) and an additive effect was observed with actinomycin D, cytarabine, doxorubicin, hydroxyurea, mercaptopurine, mitomycin C, mitoxantrone, thiotepa, vincristine and VP-16 (Su et al., *Cancer Treat Rep.* 71:619-25, 1987). Synergistic activity was also observed between $VK_3$ and doxorubicin, 5-FU, and vinblastine against nasopharyngeal carcinoma cells and with doxorubicin or mitomycin against MCF-7 breast cancer cells with pretreated with $VK_3$ (Liao et al., *Int. J. Oncol.* 17:323-8, 2000; Tetef et al., *J. Cancer Res. Clin. Oncol.* 121:103-6, 1995; Tetef et al., *Invest. New Drugs* 13:157-62, 1995). A study with rats (Gold et al., *Cancer Treat. Rep.* 70:1433-5, 1986; Lamson et al., *Altern. Med. Rev.* 8:303-18, 2003) showed that the combination of methotrexate (0.75 mg/kg/day) and menadione (250 mg/kg/day) resulted in 99% inhibition of tumor growth. Decreasing the dosage of $VK_3$ to 225 mg/kg/day resulted in 84% inhibition. In addition, circulating levels of $VK_3$ as low as 1 µM acted synergistically with methotrexate. In phase I clinical trials in humans (Akman et al., *Proc. Am. Soc. Clin. Oncol.* 7:76, 1988; Margolin et al., *Canc Chemother. Pharmacol.* 36:293-8, 1995), vitamin $K_3$ was administered at doses of 400-500 mg/day over 3-5 consecutive days without any appreciable toxicity. When $VK_3$ was administered in conjunction with mitomycin C, a maximum tolerated dose of $VK_3$ (2.5 $g/m^2$ in a 48-hour i.v. infusion) followed by mitomycin C (15 mg/m 2) every four weeks produced no hemolysis. This trial was followed by two phase II trials (Tetef et al., supra). In the first trial, 23 advanced lung cancer patients displayed a median survival of 5.5 months. Two patients had objective response lasting 3.5 to 13 months, while 26% exhibited some tumor regression. However, 30% of patients exhibited hematologic toxicity. In the second trial, 43 gastrointestinal cancer patients showed no objective response to the therapy.

Due to its fat solubility, Vitamin $K_1$ is sequestered in the liver and has been reported to disrupt blood clotting, resulting in clot formation s and the possibility of thrombotic phenomenon (Suttie, J W, "Vitamin K", In: *Handbook of Vitamins: Nutritional, Biochemical and Clinical Aspects*, L J Machlin, ed., Marcel Dekker, Inc., New York, Chap. 4, pp. 147-198, 1984). $VK_3$, is water soluble in the bisulfate form and does not appear to accumulate in appreciable amounts in the liver. Some of the present inventors and colleagues (Jamison, J. et al., *J. Nutr.* 131:158 S-60S, 2001) found no hepatotoxicity in livers of nude mice given appreciably larger doses of $VK_3$ and no effects on bone marrow or blood clotting. A long term toxicity study in CH3 inbred rats showed no appreciable toxicities in any of the animals.

The $LD_{50}$ of $VK_3$ in mice is 500 mg/Kg. No mortality was observed in mice given oral doses of 200 mg/Kg. In the same (Molitor et al., *Proc. Soc. Exp. Biol. Med.* 43:125-8, 1940) study, chronic toxicity was evaluated for oral doses of $K_3$-250, 350 or 500 mg/Kg administered daily over 30 days. The 500 mg/Kg dose was toxic. The 350 mg/Kg dose produced a marked drop in erythrocyte count and hemoglobin. The 250 mg/Kg dose did not affect either parameter or the animals' growth curves. Furthermore, in phase I clinical trials in humans (Akman et al., supra), vitamin $K_3$ has been administered at doses of 400-500 mg/day over 3-5 consecutive days without any appreciable toxicity. $VK_3$ did not produce toxicity in humans even with protracted administration at these doses. Phase I and Phase II clinical trials have been performed (Tetef et al., 1995, supra; Klenner, F. R., In: *Physician's Handbook on Orthomolecular Medicine*, $3^{rd}$ ed, R J Williams et al., eds., Pergamon, New York, pp. 51-59, 1977) using $VK_3$ in combination with mitomycin C (a drug which is far more toxic than VC) for lung and gastrointestinal cancers. In these studies, $VK_3$ was well tolerated even though it was administered i.v., generally a more toxic route (Tetef et al., supra.

Studies of Combined Treatment with VC and $VK_3$

VC was shown to accumulate in tumors, and could reverse malignant cell transformation and exert cytotoxic effects on tumor cells. VC given alone required high doses to achieve inhibitory effects. $VK_3$ inhibited growth of mammalian tumor cells in a culture, and required high dosages to achieve a desirous effect when administered alone (Noto, V et al. 1989, Cancer 63:901-6)

VC at 1 g/Kg and $VK_3$ at 10 mg/Kg were injected into mice bearing ascitic liver tumor (TLT) before or after a single treatment of several cytotoxic drugs and the effects on survival (Taper, H S et al., 1987, Int. J. Cancer 40:575-9). Combined i.p. administration of these vitamins produced a distinct chemotherapy-potentiating effect for all drugs examined, especially when injected before chemotherapy. This potentiating treatment did not increase the general and organ toxicity that accompanies cancer chemotherapy.

The use of a Vitamin C/Vitamin $K_3$ combination in conjunction with radiotherapy to treat cancer was studied (Taper, H S et al., 1996, *Anticancer Res* 16:499-504). The effect of intraperitoneal and oral pretreatment with combined VC and $VK_3$ on the single dose radiotherapy of a transplantable solid mouse tumor was investigated. Groups of mice bearing intramuscularly transplanted liver tumors, were orally and parenterally pretreated with combined VC and $VK_3$ and locally irradiated with single doses of 20, 30, or 40 Gy of X-rays. Tumor dimensions were measured twice weekly and the approximate tumor volumes in treatment groups were compared. This nontoxic pretreatment produced significant potentiation of radiotherapy induced by 20 to 40 Gy of X-rays. Combined VC with $VK_3$ was believed to constitute a redox-cycling system producing peroxide and other reactive oxygen species (ROS) to which cancer cells are selectively sensitive.

Administration of Vitamin C and Vitamin $K_3$ prior to treatment with certain chemotherapeutic agents was disclosed in Taper, H et al., 1992, *Oncology (Life Sci Adv.)* 11:19-25)

IP injection of Vitamin C and Vitamin $K_3$ was given as a pretreatment to increase tumor sensitization to the action of Oncovin (Taper, H S et al., 1992, *Anticancer Res* 12:1651-4). Combined VC and $VK_3$ therapy given i.p. 3 hours before i.p. administration of single dose of oncovin to which murine ascites liver tumor (T.L.T.) was completely resistant, was investigated. This pretreatment sensitized the tumor resistant to oncovin, whereas a separate pretreatment with either VC or $VK_3$ alone had no effect. This tumor sensitization to chemotherapy was completely suppressed by catalase pretreatment, suggesting that hydrogen peroxide generation with subsequent oxidative stress and its consequences may be involved. This sensitization was without any increased general and organ toxicity, making it a potentially addition to classical protocols of human cancer chemotherapy.

The growth inhibitory effects of VC and VK3 combined with various chemotherapeutic agents was tested in vitro on cultured human endometrial adenocarcinoma (AN3CA) cells De Loecker, W. et al., 1993, *Anticancer Res* 13:103-6. In well defined conditions of cell confluence and at the dose levels applied, a synergistic effect on growth inhibition was observed. The combined vitamins when reaching their own synergistic cytotoxicity levels frequently obscure the additional synergistic effects attributable to the chemotherapeutic agents. The formation of ROS radicals during treatment, possibly accentuated by less defined secondary mechanisms, appeared to be responsible for the observed stimulated cytotoxicity.

Action of Polyphenolic Compounds

Uncontrolled imbalance between cell proliferation and cell differentiation or cell death may result in the development of malignant or cancerous clones of cells which are commonly less differentiated than their normal counterparts. Thus, promising targets for cancer intervention are induction of (i) differentiation of pre-malignant or malignant cells into more normal cells and (ii) tumor-specific cell death during the process of carcinogenesis or tumor development. Compounds which induce differentiation or cell death are candidates for cancer chemoprevention and/or chemotherapy (Hong W K and Sporn M B, *Science*, 1997, 278:1073-7; Suh N. et al., *Anticancer Res.*, 1995, 15:233-9; Fimognari C. et al., *Biochem Pharmacol.*, 2004, 68:1133-8). In the last several years, hundreds of plant extracts have been evaluated for their potential as cancer chemopreventive agents and for their ability to induce cell death (Clement M. V. et al., *Blood*, 1998, 92:996-1002; Cooke D. et al., *Eur J Canc.*, 2005, 41:1931-40).

Many of these compounds inhibit the cellular events associated with all 3 stages of carcinogenesis (initiation, promotion and progression). One strategy employs phenolic compounds that prevent or attenuate cancer formation by blocking one or several steps in this multistage process. A non-flavonoid polyphenol, resveratrol (3,5,4'-trihydroxy-trans-stilbene, depicted below), is a typical example of such a compound.

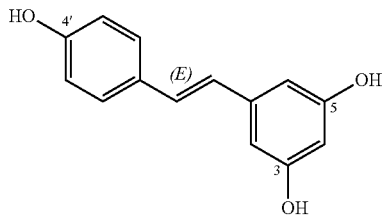 [SMILES: Oc1ccc(/C=C/c2cc(O)cc(O)c2)cc1]

Its as diverse bioactivities (Aggarwal B B et al., *Anticancer Res.*, 2004, 24:2783-2840; Fremont L., *Life Sci.*, 2000, 66:663-73) include antioxidant activity, modulation of lipid and lipoprotein metabolism, anti-platelet aggregation, vasorelaxing activity, anticancer activity, estrogenic activity. A variety of mechanisms of action for this compound have been suggested or reported including: increased levels of cell death, activation of phase II detoxification and decreased levels of cell division, DNA synthesis and inflammation (Aggarwal et al., supra; Aziz M H et al., *Int J Oncol.*, 2003 23:17-28; Dong Z., *Mutat Res.*, 2003, 523-524:145-50; Fremont L., supra; Gusman J. et al., *Carcinogenesis*, 2001, 22:1111-7; Jang M. et al., *Science*, 1997, 275:218-20; Savouret J. F. et al., *Biomed Pharmacother.*, 2002, 56:84-7; Signorelli P. et al., *J Nutr Biochem.*, 2005, 16:449-66)

Resveratrol was reported to inhibit cell proliferation and cause apoptotic cell death by modulating numerous key mediators of cell cycle and survival signaling. Depending on the concentrations, resveratrol "switched" cells between reversible cell cycle arrest and irreversible apoptosis. Specifically, resveratrol treatment blocked the cell cycle in the $G_0/G_1$, $G_1/S$ transition, S phase or $G_2/M$ phases by suppressing cyclins and their corresponding kinases, by increasing p53 levels or by inhibiting DNA synthesis. It also causes up-regulation of pro-apoptotic members of the Bcl-2 family and down-regulation of anti-apoptotic members of this family. Finally, resveratrol inhibits NF-κB and AP-1 signaling pathways, their upstream kinases and their downstream targets (including inducible cyclooxygenase-2, inducible nitric oxide synthase and matrix metallo-protease-9. Thus, resveratrol inhibits proliferation and induces cell death. (See references cited supra).

Resveratrol is considered a phytoestrogen because of its structural homology to the estrogens and it can compete with estrogens for their receptors and activate hormone receptor-mediated gene transcription. However, it can also exert an anti-estrogen action and inhibit hormone-induced carcinogenesis with the agonistic or antagonistic hormonal activity depending on the intake concentration, tissue-specific expression of estrogen receptors, cofactors present for DNA binding and different gene promoters (Aggarwal et al., supra; Fremont, supra). Likewise, resveratrol represses transcription or translation of different classes of androgen up-regulated genes via a reduction in androgen receptor (AR) content (Mitchell S H et al., *Cancer Res*, 1999, 59:5892).

While the antitumor mechanisms of resveratrol are pleiotropic, and it appears to be a promising antitumor agent in part because it affects the 3 stages of carcinogenesis, its use has been hampered by its relatively low aqueous solubility and its apparent lack of specificity to tumor cells. Resveratrol was also significantly toxic to normal cells (Aggarwal et al., supra). The present invention is directed to a distinct class of diphenyl compounds, the tolans, and their utility as anticancer agents with advantageous properties compared to resveratrol.

U.S. Pat. Nos. 6,599,945 and 7,094,809 (co-invented by one of the present inventors) disclose several hydroxytolan compounds and their uses in methods of inhibiting the formation of infectious herpes virus particles or for treating gonorrhea caused by *Neisseria gonorrhoeae*. U.S. Pat. Nos. 6,197,834 and 6,355,692 disclose certain hydroxylated stilbenes, and specifically resveratrol, for similar uses. The use of resveratrol in suppressing or treating cancer is also disclosed in U.S. Pat. No. 6,008,260.

SUMMARY OF THE INVENTION

The present invention provides a method of inhibiting the development, growth or metastasis of tumor or cancer cells, or cells of a precancerous lesion, in a subject, comprising administering to the subject in need thereof, a combination that comprises the following components:

(a) an effective growth-inhibiting or metastasis-inhibiting amount of one or more of a first compound of Formula I:

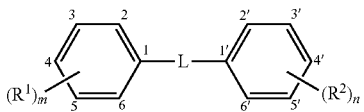

Formula I wherein:
L represents a linkage between the two phenyl rings selected from a —C≡C— acetylene linkage, a —CH=CH— ethylene linkage or a —CH$_2$—CH$_2$— ethane linkage
$R^1$ and $R^2$ are, independently substituents at any available position of the phenyl rings;
m and n are, independently, 0, 1, 2, 3, 4 or 5 representing the number of $R^1$ and $R^2$ substituents of the rings, respectively, and at least one of morn must be ≥1;
wherein $R^1$ and/or $R^2$ is:
—OH,
a halogen,
a haloalkyl group with one C atom substituted with from 1 to 3 halogen atoms,
a $C_1$-$C_6$ alkyl, $C_2$-$C_6$ alkenyl, or $C_2$-$C_6$ alkynyl group,
—OR$^3$, wherein $R^3$ is a $C_1$-$C_6$ alkyl, $C_2$-$C_6$ alkenyl, or $C_2$-$C_6$ alkynyl group; and wherein at least one occurrence of $R^1$ or $R^2$ is —OH,
with the proviso that when L is —C≡C—, the compound of Formula I is not resveratrol, and (b) an amount of a second compound which is effective in combination with the first compound to kill, or inhibit the growth of the cells, wherein the second compound is sodium ascorbate (VC); and (c) an effective amount of a third compound, which is VK$_3$ or a quinone or semiquinone analogue thereof, or an analogue or derivative of the foregoing quinone or semiquinone. In the first compound of the above method, L is preferably —C≡C—.

In one preferred embodiment, the compound of Formula I is Hydroxytolan-1, characterized by m=1 and n=1; $R^1$ is an —OH group at ring position 4; and $R^2$ is an —OH group at ring position 4'.

In another preferred embodiment, the compound of Formula I is Hydroxytolan-2, characterized by
(a) m=2 and n=1;
$R^1$ is an —OH group at ring position 3 and position 5; and
$R^2$ is an —OH at ring position 4'; or
(b) m=1 and n=2;
$R^1$ is an —OH group at ring position 4; and
$R^2$ is an —OH group at ring position 3' and position 5'.

In another preferred embodiment, the compound of Formula I is Hydroxytolan-3, wherein:
m=1 and n=1 and;
(a) $R^1$ is an —OH group at ring position 4 and
$R^2$ is a —CF$_3$ group at ring position 4', or
(b) $R^1$ is a —CF$_3$ at ring position 4; and
$R^2$ is an —OH at ring position 4'.

In another preferred embodiment, the compound of Formula I is Hydroxytolan-4 characterized by m=2 and n=2; $R^1$ is an —OH group at each of ring position 3 and position 5; and $R^2$ is an —OH group at each of ring position 3' and position 5'.

The preferred ratio of VC to the first compound in the composition that is administered to a subject is between about 50 and about 900. More preferably, the ratio is between about 100 and about 600.

As noted, the invention is directed to the above method which comprises administering to the subject the first compound and the combination of the second and the third compound, wherein the presence of VC and VK$_3$ or the VK$_3$ analogue or derivative increases the killing or growth inhibition by a statistically significant amount, at least about 10 percent over that produced by administration of the first compound alone or the combination of the first compound and VC. Alternatively, the presence of the first compound increases the killing or growth inhibition by at least about 10 percent over that produced by administration of the combination of VC and VK$_3$ or the analogue or derivative alone or the first compound alone.

The increases in killing or growth inhibition, indicated as 10% above, is preferably at least about 20%, preferably at least about 30%, more preferably at least about 40%, or at least about 50%, or at least about 60%, or at least about 70%, or at least about 80%, or at least about 90% or at least about 100%.

In one embodiment, the combination of VC and VK$_3$ is administered as a pretreatment, followed by administration of (i) the first compound or (ii) a combination of VC and the VK$_3$ or quinone or semiquinone analogue as described herein. The time between the pretreatment and the subsequent treatment may vary, and this pairing of pretreatment and treatment may be repeated on multiple occasions. In fact, in one embodiment, such repetitions of the pretreatment and treatment (i) or (ii) represent the therapeutic regimen.

In the above method, the administering of the combination of compounds results in killing of primary or metastatic tumor/cancer cells or cells of a precancerous lesion.

In the foregoing method of administering a first compound, the VC and the VK$_3$ or analogue, the first compound, the VC and the VK$_3$ or analogue may be administered by the same or by different routes, which route are preferably oral, intravenous, intranasal, intraperitoneal, topical, intrathecal, intramuscular, subcutaneous, transdermal, rectal, and intranasal.

In the above method, the tumor cells may be from a solid tumor or cancer, from a hematological malignancy, or cells of a precancerous lesion. When the tumor is a solid tumor, it may be basal cell carcinoma, bladder cancer, a brain tumor, breast cancer, bronchogenic carcinoma, colon cancer, liver cancer, lung cancer, melanoma, ovarian cancer, pancreatic cancer, prostate cancer, neuroblastoma, medulloblastoma, squamous cell carcinoma, carcinoma in situ and basal cell carcinoma. The cells being killed or inhibited are cancer cells that develop from an identifiable precancerous lesion or are cells of the precancerous lesion itself. One common precancerous lesion to which the present method is directed is actinic keratosis; others are described in more detail below. Hematological malignancies above include leukemia, lymphoma or multiple myeloma.

In the present method, the ratio of the VC to the VK$_3$ (or analogue or derivative) is preferably in the range of between about 50:1 and about 500:1, preferably between about 100:1 and about 300:1

In the above method, the amount of the VC administered orally to the subject per day is preferably between about 15 mg and 1 g per kg body weight, and the amount of the VK$_3$ or analogues or derivative administered per day is preferably between about 30 μg and about 20 mg per kg body weight.

As a result of administering the combination of compounds, as described above (a) the tumor or cancer cells being killed or inhibited are, for example, breast cancer cells, colon cancer cells, prostate cancer cells, lymphoma cells, leukemia cells, lung cancer cells, head or neck cancer cells, brain tumor cells, ovarian cancer cells, liver cancer cells, neuroblastoma cells, medulloblastoma cells, squamous cell carcinoma cells, carcinoma in situ cells or basal cell carcinoma cells; and (b) the tumor or cancer being treated in the subject is, accordingly, breast cancer, colon cancer, prostate cancer, lymphoma, leukemia, lung cancer, head or neck cancer, a brain tumor, ovarian cancer, liver cancer, neuroblastoma, medulloblastoma, squamous cell carcinoma, carcinoma in situ or basal cell carcinoma.

The treatment method results in either:

(1) a partial response, characterized as at least a 50% decrease in the sum of the products of maximal perpendicular diameters of all measurable tumor lesions without evidence of new lesions or progression of any pre-existing lesions, or (2) a complete response characterized as the disappearance of all evidence of the cancer or tumor for at least one month.

The cells being killed or inhibited may be cancer cells that developed from an identifiable or recognized precancerous lesion or they may be cells of the precancerous lesion, for example actinic keratosis. Treatment that results in the killing or inhibition of these precancerous cells will treat the actinic keratosis (or other precancerous state) and/or inhibit the development of squamous cell carcinoma from the actinic keratosis, or another form of cancer from other precancerous lesions.

DESCRIPTION OF THE PREFERRED EMBODIMENTS

Definitions and Abbreviations

A preferred ascorbate of this invention is vitamin C, abbreviated VC, which is sodium ascorbate, also abbreviated as NaVC. The chemical structure is shown below

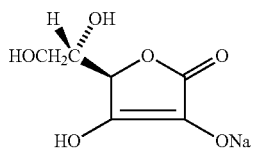

The use of a capital "C" in this abbreviated formula is not intended to mean carbon—although C does represent carbon in some "standard" chemical formulations used herein. Other ascorbates, including salts are included within the definition of ascorbate.

$VK_3$—Vitamin K3 or menadione is a polycyclic aromatic ketone, based on 1,4-naphthoquinone, with a 2-methyl substituent. Its chemical name is 2-methyl-1,4-naphthoquinone or 2-methylnaphthalene-1,4-dione, and its the chemical formula is $C_{11}H_8O_2$, molecular mass 172.18. The chemical structure is shown below

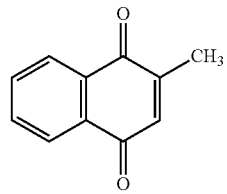

Menadione is also a vitamin precursor of $K_2$ which utilizes alkylation in the liver to yield menaquinones (MK-n, n=1-13; $K_2$ vitamers), and hence, may be classified as a provitamin. Vitamin K3 is more typically shown as "$K_3$" in the literature. However in this application, the subscripted 3 is not used to avoid confusion.

The preferred form of $VK_3$ in the present invention is the bisulfate form because it is water soluble, and does not accumulate in fat tissue of the subject. The chemical structure is shown below.

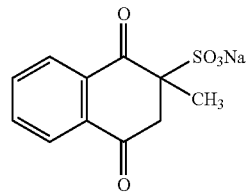

In various embodiments of the present invention, the preferred embodiment of $VK_3$ can be replaced by any quinone or semiquinone analogue of $VK_3$ that has similar biological activity, primarily in anti-cancer activity in combination with a VC or VC+hydroxytolan formulation. Thus, it should be understood that in a formulation $VC/VK_3$, the $VK_3$ can be substituted with an equimolar amount of another such quinone or hydroquinone. Benzoquinone is one example of a quinone with cancer-inhibiting activity (to several colon cancer lines growing in mice). However, the preferred quinone is Vitamin $K_3$ itself.

The abbreviations $VC/VK_3$ and $NaVC:VK_3$ using a slash or colon, represent combinations of a form of ascorbate (sodium ascorbate) or VC with a form of $VK_3$.

The present inventors have discovered that a combination of ascorbate+$VK_3$ with certain hydroxytolans compounds not heretofore known to have anticancer activity are useful in killing of cancer cells in vitro and in vivo and slowing the progression of tumor growth or metastasis. The inventors made the surprising discovery that modifying polyphenolic compounds by altering the number and/or position of the hydroxyl groups on the rings, and/or changing the chemical structure of the linkage between the aromatic rings, in particular to a —C≡C— (acetylene) linkage, results in compounds which, in combination with ascorbate and $VK_3$) kill cancer cells more rapidly and effectively while maintaining low toxicity to normal cells.

The invention also represents an improvement to the invention by some of the present inventors of a non-toxic drug combination for treating cancer using VC and menadione (synthetic $VK_3$) (U.S. Pat. No. 7,091,241). The invention disclosed herein exemplifies the surprising discovery that combining a conjugated polyhydroxylated, polycyclic compounds, particularly a hydroxylated tolan, with sodium ascorbate and $VK_3$ results in more rapid and effective killing of tumor cells.

The present invention provides combination pharmaceutical compositions or kits which when administered to a subject in need thereof, result in inhibition of cancer cell growth and induction of cancer cell death. The methods include the treatment of many forms of cancer, including bladder, prostate and ovarian cancer. The invention provides a composition and method that improves the effectiveness of certain therapeutically active phenolic compounds alone or in combination with ascorbate only.

A series of novel phenolic compounds, tolans, were evaluated for their antitumor activity in combination with ascorbate and were found to result in more rapid killing of tumor cells than with either the tolan or the ascorbate alone. The cytotoxic activity of the phenolic compounds decreased up to 20-fold when they were combined with ascorbate.

The compound resveratrol (depicted above) is a stilbene that consists of two aromatic rings linked by an ethylene bridge with two hydroxyl groups at the 3 and 5 positions of one ring and one hydroxyl group at the 4' position of the other ring. Changing the chemical structure of the linkage between the two aromatic rings led to design of novel series of hydroxytolan compounds with the desired activity when used in combination with ascorbate+$VK_3$.

The present invention therefore provides a method of affecting cancer cells in a desirable manner and thereby treating cancer using a combination of one or more members of Formula 1, preferably compounds of the hydroxytolan series described herein, plus two (or more) compounds. The second compound is preferably 5-(1,2-dihydroxyethyl)-3,4-dihydroxy-5H-furan-2-one (ascorbate or VC) and the third is $VK_3$ or a quinone or semiquinone analogue of $VK_3$. The compounds are effective at a range of ascorbate:hydroxytolan ratios, preferably between about 10 to 900. The combination may be administered orally, intravenously, intraparatoneally or intranasally (among other routes) to kill or inhibit the growth or metastasis of malignant neoplastic cells (i.e., cancer cells). The combination of compounds exhibits selective antitumor activity against human bladder, ovarian and prostate tumor cells, as exemplified herein. While the inventors do not wish to be bound by any mechanistic explanation of these effects or outcomes, nor must they be, it is believed that antitumor activity is related to redox cycling and the possible generation of peroxides and other reactive oxygen species (ROS) as well as the inhibition of tyrosine kinases and subsequent membrane lipid alterations, and DNA destruction in cancer cells which tend to be catalase-deficient.

Hydroxylated Tolans

The structural skeleton of the preferred compounds of the present invention, the hydroxylated tolans, comprises two aromatic rings joined by an acetylene bridge. The compounds preferred for the methods and uses of the present invention are described by Formula I,

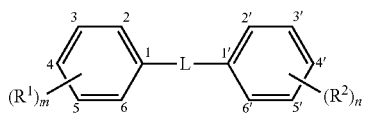

Formula I wherein:
L represents a linkage between the two phenyl rings and may be a —C≡C— acetylene linkage, a —CH=CH— ethylene linkage or a —$CH_2$—$CH_2$— ethane linkage. Most preferred is a —C≡C— linkage that characterizes tolan structures. Compounds with a —CH=CH— linkage are stilbenes, whereas-compounds with a —$CH_2$—$CH_2$— linkage are diphenylethane derivatives.

$R^1$ and $R^2$ are substituents at any available ring position;
m and n is the integer 0, 1, 2, 3, 4 or 5 representing the number of aromatic ring $R^1$ and $R^2$ substituents, respectively.

Preferred, though non-limiting examples of phenyl ring substituents $R^1$ and $R^2$ are:
OH,
halogen,
haloalkyl wherein one C atom is substituted with from 1 to 3 halogens, preferably F, Cl and Br, most preferably F, so that a most preferred haloalkyl substituent is $CH_2F$, $CHF_2$ and $CF_3$;
$C_1$-$C_6$ alkyl (referred to also as "lower alkyl"), $C_2$-$C_6$ alkenyl ("lower alkenyl"), and $C_2$-$C_6$ alkynyl ("lower alkynyl")
$OR^3$, wherein $R^3$ is lower alkyl, lower alkenyl, or lower alkynyl.

When m or n is 2 or more, the $R^1$ and $R^2$ substituents may be the same or different. For example, if m=2, the ring may be disubstituted with one —OH group and one haloalkyl group, etc.

When L is —C≡C—, at least one of $R^1$ or $R^2$ is OH (and m or n is 1)

Similar substituents of stilbenes (L is —C=C—) and diphenylethanes (L is —C—C—) of Formula I fall within the scope of this invention. In these embodiments, at least one of $R^1$ or $R^2$ is OH (and m or n is 1) so that the class of intended compounds are hydroxystilbenes and hydroxyphenyl ethanes. These may be combined with hydroxytolans and ascorbate (with or without K3) in the present compositions and such combinations used to inhibit cancer cells or treat cancer.

The most preferred tolan compounds are shown below, in terms of the features of Formula I. Each is a hydroxylated tolan in which L is a —C≡C— linkage:

(A) Hydroxytolan-1 (HT-1)
m=1 and n=1 (in Formula I);
$R^1$ is an OH group at ring position 4;
$R^2$ is an OH group at ring position 4';

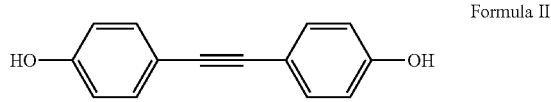 [SMILES: Oc1ccc(C#Cc2ccc(O)cc2)cc1]

Formula II

A chemical name for this compound is 4,4'-dihydroxytolan.

(B) Hydroxytolan-2 (HT-2)
m=1 and n=1 (in Formula I);
$R^1$ is an OH group at position 4 and $R^2$ is a $CF_3$ at position 4', or alternatively
$R^1$ is a $CF_3$ at position 4 and $R^2$ is an OH at position 4'.

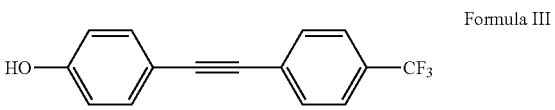

Formula III

Chemical names for this compound are 4-hydroxy-4'-trifluoromethyltolan and 4'-hydroxy-4-trifluoromethyltolan.

(C) Hydroxytolan-3 (HT-3)
m=2 and n=1 (in Formula I);

$R^1$ represents OH groups at positions 3 and 5 and $R^2$ is an OH at position 4' or, alternatively, m=1 and n=2, and $R^1$ is an OH at position 4 and $R^2$ represents OH groups at positions 3' and 5'.

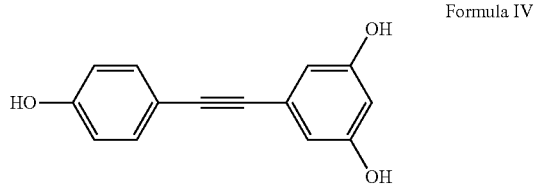 [SMILES: Oc1ccc(C#Cc2cc(O)cc(O)c2)cc1]

Formula IV

Chemical names for this compound are 3,4',5-trihydroxytolan and 3',4,5'-trihydroxytolan.

(D) Hydroxytolan-4 (HT-4)

m=2 and n=2 (in Formula I);

$R^1$ represents OH groups at positions 3 and 5 and $R^2$ represents OH groups at positions 3' and 5'

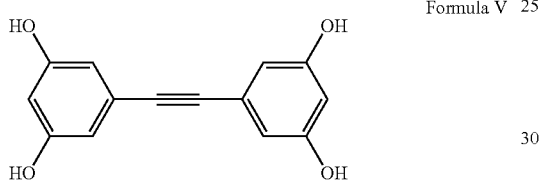

Formula V

A chemical name for this compound is 3,3',5,5'-tetrahydroxytolan.

Other compounds included within the scope of the present methods and uses are compounds of Formula I wherein L is a —C=C— or a —C—C—, and m, n, $R^1$ and $R^2$ are as described above.

The present invention is also directed to novel organic compounds among those disclosed above, and to pharmaceutical compositions that comprise these compounds along with ascorbate or ascorbate+K3. For the sake of convenience, these compounds will be referred to herein collectively as "active compounds," though it is to be understood that the other compounds with which they are combined, admixed, etc., in various embodiments disclosed herein are also "active" in a biological or pharmacological sense. As is disclosed in more detail below, the active compounds of this invention are typically admixed with one or more pharmaceutically acceptable carriers and/or excipients that are well known in the art for human and veterinary uses to make pharmaceutical or therapeutic compositions (which terms are used interchangeably).

U.S. Pat. Nos. 6,599,945 and 7,094,809 (co-invented by present inventor Tsai) disclose several of the hydroxytolan compounds and their uses in methods of inhibiting the formation of infectious herpes virus particles or for treating gonorrhea caused by *Neisseria gonorrhoeae*. Also, U.S. Pat. Nos. 6,197,834 and 6,355,692 disclose certain hydroxylated stilbenes, and specifically resveratrol, for similar uses. The use of resveratrol in suppressing or treating cancer is disclosed in U.S. Pat. No. 6,008,260.

However, none of these documents disclose or suggest the specific methods and uses of the compounds that are disclosed and claimed herein. To the extent that any specific disclosure in these publications or other publications may be considered to anticipate any generic aspect of the present invention, the disclosure of the present invention should be understood to include a proviso or provisos that exclude any such species that were previously disclosed. The aspects of the present invention which are not anticipated by the disclosure of said publications are also unobvious from the disclosure of these publications, due at least in part to the unexpectedly superior results disclosed or alleged herein. One advantage of the present invention is that the hydroxytolan and other compounds act in concert with VC (or other ascorbates, including salts), with VK3, in a combination anti-cancer composition or combination anti-cancer therapeutic method.

Approaches to Synthesis of Hydroxylated and Poly-Hydroxylated Tolans

The synthetic schemes described below are those used by the present inventors and colleagues in producing the indicated compounds. They are not intended here as exclusive approaches or schemes; more efficient methods, currently known or yet to be discovered may also be used, Rather these are illustrative of the inventor's preferred methods. A general scheme for preparing polyhydroxylated tolans is shown below.

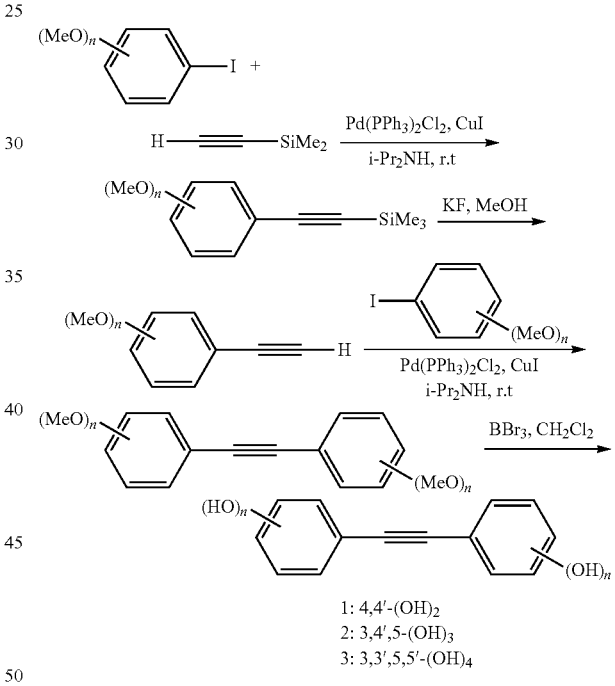

1: 4,4'-(OH)$_2$
2: 3,4',5-(OH)$_3$
3: 3,3',5,5'-(OH)$_4$

A. Synthesis of 3,5-dimethoxyiodobenzene from 3,5-dimethoxyaniline

In a 500 ml, 3-necked, round-bottomed flask equipped with a thermometer, a mechanical stirrer and an addition funnel was placed HCl (12 M, 100 ml, 1.2 mol) and crushed ice (100 g). The flask was immersed in a dry ice-Me$_2$CO cooling bath, and 3,5-dimethoxyaniline (15.3 g, 100 mmol) was added with stirring. To this cold mixture NaNO$_2$ (8.4 g, 120 mmol) in 40 ml H$_2$O was added dropwise at such a rate to maintain the temperature of the reaction mixture between −10° C. and −5° C. throughout the addition. The reaction mixture was stirred for 1 hour between 0° C. and 5° C. The red dark solution of the diazonium salt was added to a well-stirred solution of KI (83 g, 500 mmol) in 200 ml H$_2$O at room temperature. The mixture was stirred for 2 hours, then allowed to stand overnight. The resulting solution was extracted with ether (200 ml×4).

The pooled organic extracts were washed with brine (200 ml×2) and an aqueous saturated $Na_2S_2O_3$ solution (200 ml×2), dried over $MgSO_4$, filtered and concentrated to a small volume. Silica gel was added, and the mixture evaporated to dryness. This preloaded silica gel was placed on a pad of silica gel and eluted with petroleum to give 17.5 g (66%) of a colorless solid, 3,5-dimethoxyiodobenzene. $^1$HNMR ($CDCl_3$, 300 Mz): δ ppm: 6.85 (2H, d, J=2.3, Ar—H), 6.40 (1H, t, J=2.3, Ar—H), 3.76 (s, 6H, $2CH_3O$).

B. Synthesis of Arylethynyltrimethylsilanes from Ethynyltrimethylsilane and Aryl Iodides General Procedure:

To a solution of aryl methoxy substituted aryl iodide (40 mmol) in isopropylamine (250 ml) were added $Pd(PPh_3)_2Cl_2$ (0.4 mmol) and CuI (0.8 mmol), then trimethylsilylacetylene (44 mmol). The reaction mixture was stirred at ambient temperature for 2 to 4 hours under a slow stream of nitrogen. The reaction mixture was filtered and the residues were washed with ethyl acetate, and the solvent evaporated from the combined filtrates. The crude product was purified by column chromatography on silica gel using petroleum/ethyl acetate as an eluent to give the methoxy substituted arylethylyl trimethylsilanes.

(1) 2-(4-methoxyphenyl)-1-trimethylsilyl-ethyne

Purified by column chromatography on silica gel using petroleum ether as an eluent to give 2-(4-methoxyphenyl)-1-trimethylsilyl-ethyne (96% yield) as a light yellow oil.

(2) 2-(3,5-dimethoxyphenyl)-1-trimethylsilyl-ethyne

Purified by column chromatography on silica gel using petroleum ether as an eluent to give 2.2 g (94%) light yellow needles.

$T_{GC}$=5.39 ($T_{init}$=50° C.). $^1$HNMR ($CDCl_3$, 300 Mz): δ ppm: 6.6 (s, 2H, Ar—H), 6.43 (s, 1H, Ar—H), 3.77 (s, 6H, $2CH_3$), 0.24 (s, 9H, $SiMe_3$).

C. Synthesis of Methoxy Substituted Arylacetylenes

To a solution of arylethynyltrimethylsilanes (30 mmol) in methanol (30 ml) was added potassium fluoride (3.5 g, 60 mmol). The reaction mixture was stirred at room temperature for 2 hours. After removal of methanol, the product was extracted with ether (100 ml×3) and purified by chromatography on silica gel using petroleum ether as eluent to afford pure products.

(1) p-Methoxyethynylbenzene

Pale yellow oil was obtained in 92% yield. $^1$HNMR ($CDCl_3$, 300 Mz): δ ppm: 7.94 (d, 2H, J=8.98, Ar—H), 6.83 (d, 2H, J=8.55, Ar—H), 3.80 (s, 3H, $Ch_3O$), 3.00 (s, 1H—H).

(2) 3,5-Methoxyethynylbenzene

Pale yellow needle was obtained in 91% yield. $^1$HNMR ($CDCl_3$, 300 Mz): δ ppm: 7.94 (d, 2H, J=2.4, Ar—H), 6.83 (d, 2H, J=2.3, Ar—H), 3.78 (s, 6H, $2Ch_3O$), 3.94 (s, 1H—H).

D. Synthesis of Methoxytolans

General Procedure:

To a solution of methoxyethynylbenzenes (20 mmol) and methoxy substituted aryl iodide (22 mmol) in isopropylamine (120 ml) were added $Pd(PPH_3)_2Cl_2$ (0.2 mmol) and CuI (0.4 mmol). The reaction mixture was stirred at ambient temperature for 6 hours under a slow stream of nitrogen. The reaction mixture was filtered and the residues were washed with ethyl acetate and the solvent evaporated from the combined filtrates. The crude product was purified by column chromatography on silica gel using petroleum ether/ethyl acetate (9:1) as an eluent to give methoxytolans.

(1) 3,4',5-Trimethoxytolan:

A pale yellow oil was obtained in 93% yield. $^1$HNMR ($CDCl_3$, 300 Mz): δ ppm: 7.46 (d, 2H, J=8.6, Ar—H), 6.88 (d, 2H, J=8.8, Ar—H), 6.66 (d, 2H, J=2.3, Ar—H), 6.44 (t, 2H, J=2.3, Ar—H), 3.83 (s, 3H, $CH_3O$), 3.80 (s, 6H, $2CH_3O$).

(2) 3,3',5,5'-Tetramethoxytolan:

A colorless needle crystal was obtained in 85% yield. $^1$HNMR ($CDCl_3$, 300 Mz): δ ppm: 6.69 (d, 4H, J=2.3, Ar—H), 6.46 (d, 2H, J=2.3, Ar—H), 6.66 (d, 2H, J=2.3, Ar—H), 3.80 (s, 12H, $4CH_3O$).

(3) 4,4'-Dimethoxytolan:

A colorless needle crystal was obtained in 91% yield. $^1$HNMR ($CDCl_3$, 300 Mz): δ ppm: 7.46 (d, 4H, J=8.7, Ar—H), 6.87 (d, 2H, J=8.7, Ar—H), 3.82 (s, 6H, $2CH_3O$).

E. Synthesis of Hydroxytolans

General Procedure:

In a dry 250 ml, 3-necked, round-bottomed flask was placed a solution of methoxytolans (10 mmol) in anhydrous methylene chloride under $N_2$. The reaction mixture was cooled to below −20° C., and $BBr_3$ (20 mmol×the number of methoxy groups) was added by syringe. Then the reaction mixture was permitted to warm up to room temperature and stirred for over 24 hours. The reaction mixture (a reddish clear solution) was then poured into ice-water and stirred. After sufficient stirring, an aqueous $NaHCO_3$ solution was added to adjust the pH of the mixture to between 7 and 8. Then the mixture was extracted with ethyl acetate 3-4 times. The organic layer was washed with brine and dried over $MgSO_4$. Solvent was removed under reduced pressure. The red brown color crude product was purified by column chromatography on silica gel using petroleum/ethyl acetate (1:1) as an eluent to give hydroxytolans.

(1) 3,4',5-Trihydroxytolan:

A pale yellow solid was obtained in 82% yield. $^1$HNMR ($CDCl_3$, 300 Mz): δ ppm: 9.89 (s, 1H, OH), 9.45 (s, 2 h, 2-OH), 7.33 (d, 2H, J=8.65, Ar—H), 6.78 (d, 2H, J=8.63, Ar—H), 6.31 (d, 2H, J=2.2, Ar—H), 6.23 (d, 2H, J=2.2, Ar—H).

(2) 3,3',5,5'-Tetrahydroxytolan:

A pale red solid was obtained in 92% yield. $^1$HNMR ($CDCl_3$, 300 Mz): δ ppm: 9.49 (s, 4H, 4-OH), 6.33 (d, 4H, J=2.2, Ar—H), 6.25 (t, 2H, J=2.2, Ar—H).

(3) 4,4'-Dihydroxytolan:

A white solid was obtained in 93% yield. $^1$HNMR ($CDCl_3$, 300 Mz): δ ppm: 9.82 (s, 2H, 2-OH), 7.31 (d, 4H, J=8.7, Ar—H), 6.77 (d, 4H, J=8.7, Ar—H).

References: 1. Ali, M A et al., *Chem Pharm Bull*, 1992, 40:1130-6; 2. Pavia, M R et al., *Bioorg Med Chem*, 1996; 4:659-66. 3. Jeffery, T, *Tetrahedron Lett*, 1994, 35:3051-4. 4. Jeffery, T et al., *Tetrahedron Lett*, 1994, 35:4103-6. 5. Schmidt-Radde, R H et al., *J Am Chem Soc*, 1992, 114:9713-15; 6. Schumm, J. S. et al., *Angew Chem, Int Ed Eng.*, 1994, 33:1360-3; 7. Pal, M et al., *J Chem Soc Perkin Trans*, 1996, 1:449-51; 8. Bumagin, N A et al., *Russ J Org Chem*, 1996, 32:996-1000; 9. Bumagin, N A et al., *Tetrahedron Lett*, 1996, 37:897-900; 10. Meier H et al., *J Org. Chem.*, 1997, 62:4821-6.

Approaches to Synthesis of 4-Hydroxy-4'-trifluoromethyltolan

As indicated above, the synthetic schemes described below are those used by the present inventors and colleagues in producing the indicated compounds. They are not intended here as exclusive approaches or schemes, but rather are illustrative of preferred methods.

A synthetic scheme for the preparation of hydroxy-trifluoromethyltolan is shown in the diagram below. Synthetic details of the specific reaction steps are described below. Most of these reactions are readily accomplished with high yields (over 90%). All products are preferably purified by column chromatography and characterized by GC and $^1$HNMR spectrometry.

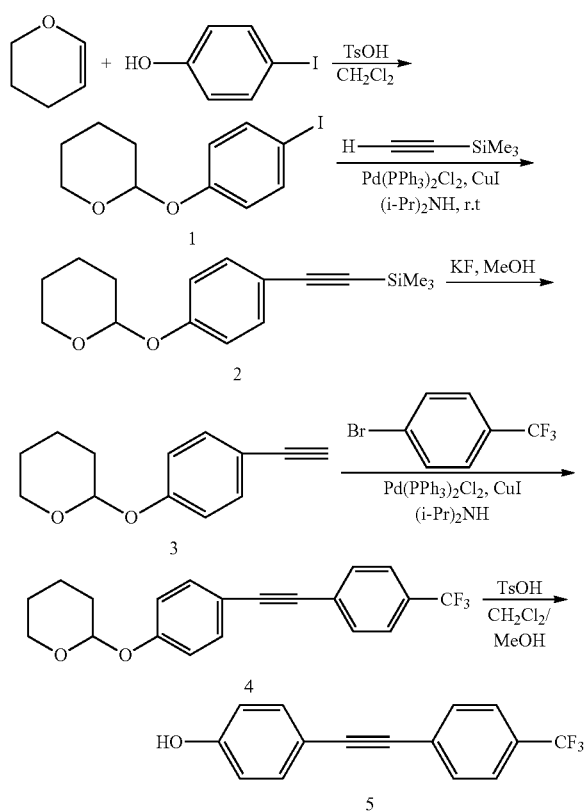

1. 1-Iodo-4-tetrahydropyranyloxybenzene 1

To a stirred solution of 4-iodophenol (11.0 g, 50 mmol) in CH$_2$Cl$_2$ (50 ml) cooled with an ice bath, dihydropyran (5.0 g, 60 mmol) was added dropwise over 10 min at 0° C. to 5° C. After the solution became clear, toluenesulfonic acid (TsOH' 10 mg) was added. The solution was stirred at 20° C. for 15 min. Then it was quenched by addition of NaHCO$_3$ (1 g) and 3 drops of water, and after stirring for 5 min at 20° C., the solvent was removed in vacuo and the residue was purified by column chromatography on silica gel with petroleum ether as eluent to give 14.0 g (92%) of 1 as colorless crystal; mp 66° C.; $\delta_H$(CDCl$_3$, 300 MHz): 7.55 (d, J=8.3, 2H, Ar—H), 6.83 (d, J=8.4, 2H, Ar—H), 5.37 (t, J=3.1, 1H, OCHO), 3.86 (m, 1H, THP), 3.59 (m, 1H, THP), 1.87~1.58 (m, 6H, THP).

2. 4-Tetrahydropyranyloxy-1-(trimethylsilylethynyl)benzene 2

To a degassed solution of compound 1 (9.12 g, 30 mmol) in diisopropylamine (180 ml) under nitrogen, Pd(PPh$_3$)$_2$Cl$_2$ (140 mg, 0.2 mmol) and CuI (78 mg, 0.4 mmol) were added. Then trimethylsilyl acetylene (3.3 g, 33 mmol) was added dropwise to this clear solution. The reaction mixture was stirred for 2 hours at room temperature. The salt formed during the reaction procedure was filtered off and washed well with ethyl acetate. The filtrate was evaporated to dryness and hydrolyzed with concentrated hydrochloric acid (5 ml), water (25 ml) and crushed ice (10 g), then extracted with ethyl acetate. The combined organic paste was washed with brine and dried with MgSO$_4$. The solvent was removed in vacuo and the residue was purified by column chromatography (petroleum ether-ethyl acetate=9:1) to give a yellow oil of 2. Yield 7.9 g (96%); $\delta_H$(CDCl$_3$, 300 MHz): 7.39 (d, J=8.7, 2H, Ar—H), 6.97 (d, J=8.6, 2H, Ar—H), 5.41 (t, J=3.1, 1H, OCHO), 3.84 (m, 1H, THP), 3.59 (m, 1H, THP), 1.86~1.61 (m, 6H, THP), 0.23 (s, 9H, 3 CH$_3$).

3. 4-Tetrahydropyranyloxyphenylacetylene 3

KF (9.3 g, 160 mmol) was added to a stirred solution of 2 (22.6 g, 80 mmol) in MeOH (150 ml). The reaction mixture was stirred at room temperature for about 4 hours. After the reaction finished (GC shows no starting material remaining), the solvent was removed under reduced pressure on a rotary evaporator. The residue was purified by column chromatography on silica gel (petroleum ether-ethyl acetate=9:1) to give a pale yellow crystals of 3. Yield 15.7 g (97%); mp 65° C., $\delta_H$ (CDCl$_3$, 300 MHz): 7.42 (d, J=8.7, 2H, Ar—H), 7.00 (d, J=8.7, 2H, Ar—H), 5.43 (t, J=3.2, 1H, OCHO), 3.87 (m, 1H, THP), 3.60 (m, 1H, THP), 2.99 (s, 1H, C≡C—H), 1.96~1.56 (m, 6H, THP).

4. 4-Tetrahydropyranyloxy-4'-trifluormethyltolan 4

A solution of 3 (12.1 g, 60 mmol) and 4-bromobenzotrifluoride (14.85 g, 66 mmol) in diisopropylamine (250 ml) was heated to 30° C. under nitrogen, and the solution was degassed. Then Pd(PPh$_3$)$_2$Cl$_2$ (210 mg, 0.3 mmol) and copper (I) iodide (114 mg, 0.6 mmol) were added to this clear solution. The reaction mixture was stirred for 2 hours at 80° C., and then cooled to room temperature. The salt formed during the reaction procedure was filtered off and washed well with ethyl acetate. The filtrate was evaporated to dryness and hydrolyzed with concentrated hydrochloric acid (10 ml), water (100 ml) and crushed ice (50 g), then extracted with ethyl acetate. The combined organic paste was washed with brine and dried over MgSO$_4$. The solvent was removed in vacuo and the residue was purified by column chromatography (petroleum ether-ethyl acetate=9:1) to give a pale yellow crystals of 4. Yield 16.6 g (80%); mp 112~113° C.; $\delta_H$ (CDCl$_3$, 300 MHz): 7.59 (s, 4H, Ar—H), 7.48 (d, J=8.7, 2H, Ar—H), 7.04 (d, J=8.7, 2H, Ar—H), 5.46 (t, J=3.1, 1H, OCHO), 3.89 (m, 1H, THP), 3.62 (m, 1H, THP), 1.86~1.62 (m, 6H, THP).

5. 5-Hydroxy-4'-trifluoromethyltolan 5

Compound 4 (13.84 g, 40 mmol), CH$_2$Cl$_2$ (75 ml) and MeOH (125 ml) were placed in a 250 ml round-bottomed flask, then TsOH (0.4 g, 0.4 mmol) was added. The reaction mixture was stirred at 30° C. for 1 hour. When the reaction was finished (TLC showed no starting material remaining), the solvent was removed by rotary evaporation and the residue was dissolved in EtOAc and filtered through silica gel. The solvent was removed and the solid was recrystallized from solvents of ethyl acetate and hexane (1:5) to give a pale yellow crystal 9.5 g (90%), mp 131-132° C., $\delta_H$ (CDCl$_3$, 300 MHz): 7.59 (s, 4H, Ar—H), 7.44 (d, J=8.7, 2H, Ar—H), 6.82 (d, J=8.7, 2H, Ar—H), 5.16 (s, 1H, OH).

References: Shen, D. et al., *J Matter Chem.*, 1999, 9:661. 2. Praefcke, K et al., *Angew. Chem. Int. Ed. Engl.*, 1990, 29:177; 3. Bouchta, A. et al., *Liq Crystals*, 1992, 12:575; 4. Hsieh, C J et al., *Liq. Crystals*, 1994, 16:469

Synthesis for other tolans, stilbene derivatives and diphenylethane derivatives utilize methods that are known in the art, and are thus not reiterated here.

Vitamin C/Ascorbate

The chemical structure of sodium ascorbate was shown in the background section. Preparation of this Compound is routine in the art.

Vitamin $K_3$ and Derivatives

The combination therapy of the present invention includes $VK_3$ or an active quinone or hydroquinone analogue of $VK_3$, such as benzoquinone. Thus, when referring to Vitamin $K_3$ or $K_3$ or menadione, herein, the terms are intended to include these quinone or semiquinone analogues.

Also included is a method of inhibiting metastasis of cancer cells sensitive to the effects of a $VC/VK_3$ combination which comprises administering to a subject in need thereof, a combination of a hydroxytolan compound, VC and $VK_3$ or an active quinone or semiquinone analogue of $VK_3$, wherein the combination is administered in an amount synergistically effective to inhibit such metastasis.

Cancer, Tumors and Neoplastic Cells

The methods of the present invention employ combination therapy with one or more of the active diphenol compounds disclosed herein, preferably hydroxytolans, administered together with VC/ascorbate compound and $VK_3$. Such treatment attenuates, retards, inhibits, decreases, impedes, or reverses, etc., tumor development and growth, at least in part by killing the cancer cells. The ability of the present compositions and methods to act in a preventative manner results in substantially reduced size of tumor, and even its elimination, thereby preventing, attenuating or reversing any pathological effects of the tumor or cancer on the patient.

Also intended is the use of the present formulations and combination therapies in conjunction with yet other conventional cancer treatment, including chemotherapy, radiotherapy, biotherapy and surgery or any combination thereof.

When used as a supplemental treatment, the method of the present invention, because of its nontoxic nature, can be initiated before the start of conventional treatment, continued during intervals between subsequent recurring rounds of conventional therapy, and may be continued after cessation of conventional therapy.

Thus, the present methods are directed to the killing of neoplastic of cancer or metastatic cells and the treatment of any of a number of cancers, including solid tumors and leukemias and lymphomas. A "neoplastic" cell exhibits uncontrolled proliferation. Generally, progeny of a neoplastic cell are also neoplastic and do not undergo terminal differentiation in vivo in response to physiological signals. Neoplastic cells include cells that are also described as cancer cells, cancerous cells and transformed cells. Neoplastic cells may occur as single, isolated cells in the body or aggregated, either homogeneously (with other neoplastic cells) or heterogeneously, with other cell types, as in a tumor or other collection of cells. A "tumor" is a collection of cells (neoplastic or otherwise) in which at least some of the cells are in physical contact with one another, typically by sharing a common extracellular matrix. The terms "cancer," "carcinoma," and "cancerous" when used herein refer to or describe the physiological condition, preferably in a mammalian subject, that is typically characterized by unregulated, neoplastic cell growth.

Treatment of cancer, a tumor, a premalignant disease or a hyperproliferative disorder by the present compositions includes the killing, inhibiting or slowing the growth of the relevant target cells, or inhibiting the increase in size of a tumor or cancerous growth. This includes reducing cell numbers, or preventing metastasis. "Treatment" as used herein is not meant to imply total cure or disappearance of cancer of a growing tumor. "Treatment" or "treating" is also intended to include prophylaxis, i.e., the prevention of development of a tumor or cancer, either primary, metastatic or recurrent.

Malignant and metastatic diseases and conditions (tumors and cancer) which can be treated in accordance with the present invention include, but are not limited to, solid tumors, e.g., carcinomas, sarcomas, lymphomas and other malignant or nonmalignant tumors such as those listed below. For a review of such disorders, see any textbook of clinical oncology, e.g., Cancer: Principles & Practice of Oncology, $5^{th}$ Ed. (DeVita, V. et al., eds), Philadelphia: Lippincott-Raven Publishers, 1997 or later edition). Examples of types of cancers that are successfully treated by the present compositions and methods are presented in the list below and in Table 1, below, which is not intended to be limiting. Thus the present invention is directed to the treatment of pancreatic carcinomas, renal cell carcinomas, small cell lung carcinoma, non-small cell lung carcinoma, prostatic carcinoma, bladder carcinoma, colorectal carcinomas, breast, ovarian, endometrial and cervical cancers, gastric adenocarcinoma, primary hepatocellular carcinoma, genitourinary adenocarcinoma, thyroid adenoma and adenocarcinoma, melanoma, retinoblastoma, neuroblastoma, mycosis fungoides, pancreatic carcinoma, prostatic carcinoma, bladder carcinoma, myeloma, diffuse histiocytic and other lymphomas, Wilms' tumor, Hodgkin's disease, adrenal tumors (adrenocortical or adrenomedullary), osteogenic sarcoma, soft tissue sarcoma, Ewing's sarcoma, rhabdomyosarcoma and acute or chronic leukemias, islet cell cancer, cervical, testicular, adrenocortical, or adrenomedullary cancers, choriocarcinoma, embryonal rhabdomyosarcoma, Kaposi's sarcoma.

TABLE 1

| Nonlimiting List of Cancers/Tumors |
|---|
| acoustic neuroma |
| Adenocarcinoma |
| angiosarcoma |
| Astrocytoma |
| basal cell carcinoma |
| bile duct carcinoma |
| bladder carcinoma |
| breast cancer |
| bronchogenic carcinoma |
| cervical cancer |
| Chondrosarcoma |
| Choriocarcinoma |
| colorectal carcinomas |
| Craniopharyngioma |
| Cystadenocarcinoma |
| Embryonal carcinoma |
| Endotheliosarcoma |
| ependymoma |
| esophageal carcinoma |
| Ewing's tumor |
| Fibrosarcoma |
| gastric carcinoma |
| Glioma/glioblastoma |
| Head and neck cancers |
| Hemangioblastoma |
| Hepatocellular carcinoma |
| Hepatoma |
| Kaposi's sarcoma |
| leiomyosarcoma |
| liposarcoma |
| Lung carcinoma |
| lymphangiosarcoma |
| lymphangioendotheliosarcoma |
| Lymphoma |
| Leukemia |
| medullary carcinoma |
| medulloblastoma |
| Melanoma |
| meningioma |

TABLE 1-continued

Nonlimiting List of Cancers/Tumors mesothelioma
Multiple myeloma
Myxosarcoma
Nasopharyngeal carcinoma
Neuroblastoma
Oligodendroglioma
osteogenic sarcoma
ovarian cancer
pancreatic cancer
papillary adenocarcinomas
Pinealoma
prostate cancer
renal cell carcinoma
Retinoblastoma
Rhabdomyosarcoma
sebaceous gland carcinoma
Seminoma
small cell lung carcinoma
squamous cell carcinoma
sweat gland carcinoma
Synovioma
testicular tumor
Thyroid cancer
Wilms' tumor The methods and combinations of compositions of the present invention are also used to treat precancers and prevent their progression to cancer, as indicated above.

During cancer progression, distinctive lesions occur that persist for a time and that they have a set of characteristic properties that permit them to be detected, diagnosed, prevented, and treated. A recent publication (Berman, J et al., 2006, *Cancer Detec Prevent.* 30:387-94, incorporated by reference in its entirety) summarized results of a consensus conference held in 2004 sponsored by the National Cancer Institute to develop a newer definition of precancers. The participants developed a working definition for the precancers that clinicians and researchers can use to distinguish precancers from non-neoplastic changes and from other types of changes that might be encountered during "cancer progression." This definition modified and made more general an earlier definition that had been proposed for endometrial intraepithelial neoplasia (e.g., Mutter G L et al., In: Crum C P et al., eds. *Diagnostic gynecologic and obstetric pathology.* Philadelphia: Saunders, 2006). All of the following five criteria were considered to apply in defining precancer:

(1) Evidence exists that the precancer is associated with an increased risk of cancer.
(2) When a precancer progresses to cancer, the resulting cancer arises from cells within the precancer.
(3) A precancer is different from the normal tissue from which it arises.
(4) A precancer is different from the cancer into which it develops, although it has some, but not all, of the molecular and phenotypic properties that characterize the cancer.
(5) There is a method by which the precancer can be diagnosed.

These five criteria were considered to represent the minimal set of conditions, necessary and sufficient, for a lesion detected by any method to be considered a precancer. All of the criteria must apply concurrently. The different kinds of precancers may vary in every biologic feature except those specified in the definition (identifiable lesions that precede the development of cancer). It is notable that the definition has no required morphologic criteria. Most earlier definitions of precancers presumed specific morphologic features that permitted them to be recognized. The specific diagnostic criteria are not limiting, so that cytogenetic, molecular, and even behavioral (phenotypic) properties are considered. A number of issues remained open after this conference.

While a number of human cancers have an identifiable precancer (see Table 2 below) it is expected that information regarding putative nonepithelial precancers will emerge as new genomic, proteomic, and functional data are generated in these non-epithelial models. Although the best examples of precancers today are epithelial, the definition adopted above is sufficiently general and open ended to be applicable to non-epithelial precancers.

Precancers are not obligate lesions preceding cancers. For example, adenomas are precancerous lesions that may lead to the development of colorectal carcinoma. However, it is not known whether every colorectal carcinoma is preceded by an adenoma, or whether some cases of colorectal carcinoma arise ab initio from a single transformed cell that appeared within a population of normal cells, and which was not associated with an identifiable precancerous lesion. Obviously, the practical benefits of precancer detection and therapy are diminished when the interval between the appearance of a precancer and its progression to an invasive cancer is brief.

At the histological level, epithelial precancers are relatively easy to define and to diagnose. Most are characterized as foci of atypical cells confined within the normal anatomic boundary of the epithelial compartment (i.e., the basement membrane). Atypical cells that have penetrated the basement membrane are considered malignant because they are invasive. The term "intraepithelial neoplasia" describes these lesions and includes specific criteria for their diagnosis. Despite certain open issues, precancers have distinctive biological properties that serve to separate them from the cancers, even if there is no intraepithelial compartment that can be examined for invasion. Some of the general properties of precancers that would apply to non-epithelial and epithelial precancers are as follows.

TABLE 2

Most frequently occurring cancers of man have identifiable precancerous lesions*

| Identifiable Precancerous Lesion | → Cancer that develops |
|---|---|
| Actinic keratosis/squamous cell carcinoma in situ | → Squamous carcinoma of skin |
| Adenocarcinoma in situ of endocervix | → Invasive adenocarcinoma of endocervix |
| Atypical ductal dysplasia/carcinoma in situ | → Invasive ductal carcinoma of breast |
| Atypical endometrial hyperplasia | → Endometrioid adenocarcinoma |
| Barrett's esophagus/dysplasia | → Esophageal adenocarcinoma |
| Bronchial squamous dysplasia/carcinoma in situ | → Squamous cell carcinoma of the lung |
| Cervical intraepithelial neoplasia | → Cervical squamous carcinoma |
| Colorectal adenoma | → Colorectal carcinoma |
| Gallbladder dysplasia/carcinoma in situ | → Invasive carcinoma of the gallbladder |

TABLE 2-continued

Most frequently occurring cancers of man have identifiable precancerous lesions*

| Identifiable Precancerous Lesion | → Cancer that develops |
|---|---|
| Gastric dysplasia/carcinoma in situ | → Gastric adenocarcinoma |
| In situ medullary thyroid carcinoma | → Medullary thyroid carcinoma |
| In situ melanoma | → Melanoma |
| Intratubular germ cell neoplasia | → Invasive germ cell neoplasms |
| Myelodysplastic syndrome | → Leukemia |
| Oral dysplastic leukoplakia | → Oral squamous carcinoma |
| Pancreatic intraepithelial neoplasia | → Pancreatic adenocarcinoma |
| Progressive transformation of germinal centers | → Hodgkin's disease |
| Prostatic intraepithelial neoplasia | → Prostatic adenocarcinoma |
| Urothelial carcinoma in situ | → Invasive urothelial carcinoma |

Henson DE et al., eds. *Pathology of incipient neoplasia*. 3rd ed. New York: Oxford University Press, 2001; Greenberg AK et al., 2002, Respir Res. 3: 20-30; Bostwick DG et al., 2004, High-grade prostatic intraepithelial neoplasia. Mod Pathol 17: 360-79.; Henson DE et al., In: Kelloff G et al., eds., *Cancer chemoprevention strategies for cancer chemoprevention*, vol. 2. Totowa, NJ: Humana Press, 2005: pp69-96.; /Hruban RH et al., 2004, Am J Surg Pathol 28: 977-87.

Regression— not all precancers progress to cancer. The regression rate of all precancerous lesions of bronchial epithelium was found to be 54% in one study (Breuer R H et al., 2005, *Clin Cancer Res* 11:537-43) and was unrelated to various risk factors. In cervical intra-intraepithelial neoplasia, on the other hand, lack of progression or regression was directly related to the degree of cytologic atypia, mitotic activity, and type of human papillomavirus infection (Nasiell K et al., 1983, *Obstet Gyneco*; 61:609-14). Most in situ neuroblastomas do not evolve into clinically apparent tumors (Henson et al., 2001, supra). In some nonepithelial malignant tumors, regression may be common (Krikorian J G et al., 1980, *Cancer* 46:2093-9). For instance, clinical regression was reported in 30% of cases of untreated follicular lymphomas (Horning S J et al., 1984 *N Engl J Med* 311:1471-5). Regression has rarely been reported in testicular germ cell neoplasms, neuroblastoma, melanoma, and other invasive cancers (Simpson K et al., 2007, *Ann Diag Pathol* 11:97-102). Regardless of the method of detection the lesions designated as precancers are often members of a biologically heterogeneous group comprised of some lesions that progress to cancer and other lesions, usually the majority, that persist without developing into invasive cancer or that regress. At present, it is not possible to distinguish precancers that progress from those (of similar morphology) that do not progress or that regress.

Precancer Progression:

Even though it is difficult to distinguish precancers that progress from those that do not progress, on a practical level again, epithelial precancers that do progress usually show greater cytologic atypia, more mitotic activity, and more genetic abnormalities than those that persist or regress. If a proliferative lesion typically transforms, over time, into a more aggressive lesion with identifiable features of the malignant phenotype not observed in the original lesion, this would be another reason to suspect that the original lesion is a precancer. Examples of non-epithelial proliferative lesions that occasionally transform into a more aggressive and morphologically malignant tumor are shown in Table 3.

Multiplicity of Lesions:

Carcinogenic agents often produce multiple precancers in animal models. Over time, some of these develop into cancers (McDonnell T J et al., 1991, *Nature* 349:254-6; Solt D B et al., 1977, *Am J Pathol* 88:595-618; Kirkpatrick C J et al., 2000, *Am J Pathol* 156:1455-67). The occurrence of multiple precancers seems also to exist in humans. An individual with hundreds of actinic keratoses is more likely to have one or more squamous cell carcinomas than an individual with only a few keratoses. An individual with hundreds of nevi will likely have a smaller number of atypical nevi and a very small number of malignant melanomas. Colon adenomas that develop in familial adenomatous polyposis are often synchronous and multiple, but it is unusual to find patients with multiple colon carcinomas. When a proliferative lesion is multiple, it may well be a precancer. A number of human cancers are components of inherited neoplastic syndromes, such as MEN type IIa. Patients with this syndrome develop a precancerous lesion, known as C-cell hyperplasia or medullary thyroid carcinoma in situ (Albores-Saavedra J et al., 2001, *Endocr Pathol* 12:365-77). This precancerous lesion is often multicentric, nearly always bilateral, and can be detected by identification of the specific RET germline mutation. Other genetically determined syndromes are characterized by precancerous lesions that are multicentric and diagnosed preoperatively by genetic testing.

Chronologic Precedence:

Progression of precancers to cancer, if it occurs, takes place over time. Thus, for any given precancer, the average age of individuals in whom the precancer occurs should be younger than the average age of individuals in which the developed cancer occurs. The property of chronological precedence seems to be an inescapable truth. If populations were screened at regular intervals, and if there were methods to reliably detect precancers and cancers, it might be feasible to use epidemiologic data to determine the chronologic precedence of precancers. With few exceptions, this type of study has not been carried out.

TABLE 3

Examples of non-epithelial proliferative lesions that occasionally transform into a more aggressive and morphologically malignant tumor

| Lesion | → Malignant Tumor |
|---|---|
| Fibrous dysplasia | → Osteosarcoma |
| Neurofibroma | → Malignant peripheral nerve sheath tumor |
| Osteochondroma | → Chondrosarcoma of bone |
| Progressive transformation of germinal centers | → Lymphocyte-predominant Hodgkin's disease |

Pharmaceutical and Therapeutic Compositions and their Administration

The compounds that may be employed in the combination pharmaceutical compositions of the invention include all of the compounds of Formula I described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

A composition of this invention may be active per se, or may act as a "pro-drug" that is converted in vivo to the active form.

The compounds in the composition, as well as the pharmaceutically acceptable salts thereof, may be incorporated into convenient dosage forms, such as capsules, impregnated wafers, tablets or injectable preparations. Solid or liquid pharmaceutically acceptable carriers or excipients are preferably employed. The preparations which can be administered orally or which can be used for the preferred other modes of administration, including suitable solutions for administration by injection or infusion, preferably contain from about 0.01% to 15%, preferably from about 0.1% to 10% by weight or by volume of active compound(s), together with the carrier or excipient.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Gennaro, A. E., *Remington: The Science and Practice of Pharmacy*, Lippincott Williams & Wilkins Publishers; 2003 (or a later edition).

The pharmaceutical preparations are made using conventional techniques of pharmaceutical chemistry and formulation involving such steps as mixing, granulating and compressing, when necessary for tablet forms, or mixing, filling and dissolving the ingredients, as appropriate, to give the desired products for the various routes of administration described herein including oral and parenteral. The pharmaceutical compositions may contain minor amounts of nontoxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, as well as humans.

The term "systemic administration" refers to oral or parenteral administration of a compound described herein, in a manner that results in the introduction of the compound into the subject's circulatory system or otherwise permits its spread throughout the body, such as intravenous (i.v.) injection or infusion, intramuscular, rectal or transdermal administration. The present invention further includes the following routes of administration: subcutaneous, topical, intradermal, intraarterial, intraperitoneal, intralesional including intratumoral, intrathecal, intracranial, intraarticular, intravesical, intraprostatic, intrapericardial, intrapleural, intratracheal, intranasal, intravitreal, vaginal, mucosal, and the like. Administration may be local, regional, or systemic. Administration may be by aerosol (lung instillation), injection, infusion, continuous infusion, localized perfusion bathing target cells directly or via a catheter and/or lavage.

"Regional" administration refers to administration into a specific, and somewhat more limited, anatomical space, such as intraperitoneal, intrathecal, subdural, or to a specific organ. Other examples include intravaginal, intrapenile, intranasal, intrabronchial (or lung instillation), intracranial, intra-aural or intraocular. It is noted that intrathecal administration is not intended to be limited to a more commonly used definition of intracranial spaces. The compounds may be injected or instilled directly into a cavity or space ("thecum") surrounding an organ or body region in which a tumor is present or is causing fluid accumulation. Such spaces include the pleural space, peritoneum, subarachnoid space or dural space, or pericardial space. The generic term for administration into a sheath encasing an organ is termed "intrathecal," defined in Dorland's Medical Dictionary 29$^{th}$ Edition, W B Saunders (2000) and Stedman's Medical Dictionary, 27$^{th}$ Edition, Lippincott, Williams & Wilkins (2000) as meaning "within a sheath."

"Local administration" refers to administration of a composition or drug into a more limited or circumscribed anatomic space, such as intratumoral injection into a tumor mass or subcutaneous (s.c.) injection.

One of skill in the art will understand that local administration or regional administration often also results in entry of the active compound into the circulatory system, so that such routes, e.g., s.c., may result in systemic administration of the compound.

The preparation of the present pharmaceutical compositions are known to those of skill in the art (See for example, Gennaro, A E., *Remington: The Science and Practice of Pharmacy*, Lippincott Williams & Wilkins Publishers; 2003 (or latest edition); *Pharmaceutical Analysis*, Watson D, ed. (1999) (or later edition), Harcourt Pub Ltd, London). For human administration, it will be understood that the preparations meet the sterility, pyrogenicity, general safety and purity standards required by FDA Office of Biological Standards and other relevant regulatory bodies.

Injectable or infusible preparations can be prepared in conventional forms, either as solutions or suspensions, solid forms suitable for dissolution or suspension in liquid prior to injection or infusion, or as emulsions. Though the preferred routes of administration are systemic, such as i.v., the present pharmaceutical composition may be administered topically or e.g., as an ointment, cream or gel, or transdermally or rectally, e.g., as a suppository.

For topical application, the compound may be incorporated into topically applied vehicles such as a salve or ointment. The carrier for the active ingredient may be either in sprayable or nonsprayable form. Non-sprayable forms can be semi-solid or solid and comprise a carrier indigenous to topical application and have a dynamic viscosity preferably greater than that of water. Suitable topical formulations include, but are not limited to, solutions, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like. Oils of animal or plant origin such as peanut oil, mineral oil, soybean oil, or sesame oil, corn oil, or synthetic oils may be added. The liquid form of topical pharmaceutical composition may be in the form of a solution of physiological saline, with dextrose or other saccharide, or glycols such as ethylene glycol, propylene glycol or polyethylene glycol. The preparation of such topical composition having suitable pH, isotonicity, and stability, is within the skill in the art.

Also suitable for topic application as well as for lung instillation are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

The topical compositions of the present invention are particularly useful to treat cancerous or pre-cancerous skin conditions. For preferred topical applications, especially for humans, an effective amount of the compound is administered to an affected area, e.g., skin surface, mucous membrane, eyes, etc. This amount will generally range from about 0.01 mg to about 10 mg per application, depending upon the area to be treated, the severity of the symptoms, and the nature of the topical vehicle employed.

The topical composition may further contain other agents which enhance the uptake or activity of the active compound of the invention or complement its activity in treating the disease. Such additional factors and/or agents may be included in the pharmaceutical composition to produce a synergistic effect with the active compound or to minimize side effects.

Other pharmaceutically acceptable carriers for the compositions of the present invention, preferably the topical compositions, are liposomes. These are pharmaceutical compositions in which the active compound is preferably combined with amphipathic agents such as lipids which exist in aggregated form as micelles, insoluble monolayers, liquid crystals, or lamellar layers in aqueous solution. The hydrophobic layer, or lipidic layer, generally, but not exclusively, comprises phospholipids such as lecithin/lysolecithin and sphingomyelin, monoglycerides, diglycerides, sulfatides, steroids such as cholesterol, saponin, bile acids, and more or less ionic surface active substances such as dicetylphosphate, stearylamine or phosphatidic acid, and/or other materials of a hydrophobic nature. Those skilled in the art will appreciate other suitable embodiments of the present liposomal formulations. Preparation of such liposomal formulations is within the level of skill in the art.

Therapeutic compositions for treating tumors and cancer may comprise, in addition to the present compound, one or more additional anti-tumor drugs or agents, such as mitotic inhibitors, e.g., vinblastine; alkylating agents, e.g., cyclophosphamide; folate inhibitors, e.g., methotrexate, antimetabolites, e.g., 5-fluorouracil and cytosine arabinoside, intercalating antibiotics, e.g., adriamycin and bleomycin; enzymes or enzyme inhibitors, e.g., asparaginase, topoisomerase inhibitors such as etoposide; or biological response modifiers, e.g., cytokines and interferons. In fact, pharmaceutical compositions comprising any known cancer therapeutic in combination with the compounds disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents.

The pharmaceutical compositions of the present invention may, if desired, be presented in a pack or dispenser device which may contain one or more unit dosage forms containing the active compound. The pack may, for example, comprise metal or plastic foil, such as a blister pack in the case of pills or capsules. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In the present methods, the compounds can also be administered in sustained release forms or from sustained release drug delivery systems. A description of representative sustained release materials can be found in Gennaro, supra.

The therapeutic dosage administered is an amount which is therapeutically effective in treating the target disease, preferably cancer, as is known to or readily ascertainable by those skilled in the art. The dose is also dependent upon the age, health, and weight of the recipient, kind of concurrent treatment(s), if any, the frequency of treatment, and the nature of the effect desired. Effective doses or amounts can be determined in view of this disclosure by one of ordinary skill in the art by carrying out routine trials with appropriate controls. Comparison of the appropriate treatment groups to the controls will indicate whether a particular dosage is effective. An effective amount of the compound to treat a tumor or cancer is an amount sufficient to achieve a steady state concentration in vivo which results in treatment, healing, prevention, prophylaxis, amelioration, or reduction in the symptoms. In the art of tumor or cancer therapy, this preferably refers to a measurable reduction in a relevant parameter of disease such as attenuating or reversing growth of a primary or a metastatic tumor, reduction in tumor load, preventing or reducing recurrence or metastasis of a primary tumor, or a measurable prolongation of disease-free interval or of survival. For example, a reduction in tumor growth in 20% of patients is considered efficacious or effective (Frei III, E., *The Cancer Journal* 3:127-136 (1997)). However, an effect of this magnitude is not considered to be a minimal requirement for the dose to be effective in accordance with this invention. Therapeutic or treatment responses can be complete response (CR) or partial responses (PR). DeVita et al., (supra). Table 4 below shows accepted definitions, established by the International Union Against Cancer:

TABLE 4

| RESPONSE | DEFINITION |
|---|---|
| Complete response (CR) | Disappearance of all evidence of disease |
| Partial response (PR) | >50% decrease in tumor burden; no new lesions; no progression of pre-existing lesions |

TABLE 4-continued

| RESPONSE | DEFINITION |
|---|---|
| Less than partial response (<PR) | 25-50% decrease in tumor size, stable for at least 1 month |
| Stable disease | <25% reduction in tumor size; no progression or new lesions |
| Progression | >25% increase in size of any one measured lesion or appearance of new lesions despite stabilization or response of disease in other measured sites |

"Tumor burden" is the sum of the products of the areas (products of maximal perpendicular diameters) of each measurable lesion. As used herein, the tumor burden may either (a) stabilize, which is the failure of the tumor burden to increase, i.e., no new lesions and no increase in the area of any one lesion, or (b) decrease A preferred dose of the polyphenolic compound, preferably hydroxytolan, as a component of the combination therapeutic for treating a tumor-bearing subject, preferably a mammal, more preferably human, is an amount of up to about 10 mg/kg body weight of the tolan compound. A typical single dosage of the compound is between about 10 µg/kg and about 5 mg/kg body weight. For topical administration, dosages of about 0.1-15% concentration (by weight) of the compound, preferably 1-10%, are suggested. A total daily dosage of about 1 mg to about 350 mg is preferred for intravenous administration. The foregoing ranges are, however, suggestive, as the number of variables in an individual treatment regime is large, and considerable excursions from these preferred values are expected. Although a single application or administration of the present compounds may be sufficient to ameliorate some measurable symptoms or the pathologies, it is expected that multiple doses by one or more routes, possibly for periods as long as weeks, months and longer, will be required for the desired therapeutic outcomes.

The preferred ratio of the VC or ascorbate homologue to the first active compound (preferably a hydroxylated tolan) is between about 50 and 900, more preferably between about 100 and 600.

For oral administration, the dose of Vitamin C or ascorbate homologue may range from about 15 mg to about 0.1 g per Kg body weight per day.

The dose range of active hydroxytolan and ascorbate may be determined using the ratios given above.

For i.v. or i.p, administration, the dose of the Vitamin C or ascorbate homologue preferably in the range of 7 mg/Kg/day to about 3 g/Kg/day. In a preferred embodiment, the dose is about 30 mg/Kg/day to 1 g/Kg/day. The dose of the active compound, preferably a hydroxytolan, may be determined using the ratios shown above.

The combination can be administered by any suitable manner or route, preferably e.g., orally, i.v. or i.p. The two agents can be delivered by different routes, e.g., injection of the hydroxytolan or related compound and oral administration of the ascorbate. In a preferred embodiment, both oral and intravenous administration are utilized during the course of treatment.

The amounts of ascorbate/VC and $VK_3$ in relation to the hydroxytolan compound are determined using the parameters provided above. The amounts and ratios of $VK_3$ to VC are discussed in U.S. Pat. No. 7,091,241, and below.

EXAMPLE I

Combination of Hydroxytolan Ascorbate and $VK_3$ Against Human Bladder Cancer Cells VC (ascorbic acid) and menadione sodium bisulfate ($VK_3$) were dissolved in culture medium (MEM) as stock solutions of 4 mM VC,), 0.5 mM $VK_3$, and a mixture of 4 mM VC/0.4 mM $VK_3$.

For VC alone, HT-1 alone, or the VC/HT-1 combination, a series of 12 two-fold dilutions of each compound or the combination in MEM were prepared to generate a 12 point cytotoxicity curve. After 1 or 2 days of incubation at 37° C. in humidified $CO_2$ in air, a colorimetric MTT assay (see below) was performed to evaluate the number of remaining viable T24 cells in each well.

The hydroxytolan HT-1 was dissolved in DMSO as 2 mM stock and was then subsequently diluted in MEM so that the final DMSO concentration in any well was <1%. Doubling dilutions of this stock solution were carried out as above.

For pretreatment with the VC:$VK_3$ combination, the $VK_3$ concentrations were adjusted to yield VC:$VK_3$ ratios ranging from 100:1 to 500:1, and the ratio of 100:1 was used in the study shown below.

A study was conducted to test the effect of pretreatment with VC:VK3 on killing tumor cells in vitro. T24 human bladder cancer cells in flat bottom microwells were exposed to a mixture of 150 µM VC and 1.5 µM $VK_3$ (100:1 ratio) for 2 h. The medium containing the VC:VK3 mixture was then removed from the wells, the cells were washed with PBS and medium containing serial two-fold dilutions of VC:HT-1 at a ratio of 200:1 was added to the wells. This assay measures the formation of a colored product produced from a chromogenic substrate, the tetrazole 3-[4,5-dimethylthiazol-2-yl]-2,5 diphenyltetrazolium bromide ("MTT"). The yellow MTT is reduced to purple formazan in the mitochondria of living cells. A solubilization solution (typically dimethyl sulfoxide or sodium dodecyl sulfate (SDS) in dilute hydrochloric acid) is added to dissolve the insoluble purple formazan product into a colored solution. The absorbance of this colored solution is quantified by measuring at a certain wavelength (usually between 500 and 600 nm) by a spectrophotometer. The amount of purple formazan product generated is proportional to the number of viable cells (Mosmann, T., 1983, *J. Immunol. Meth.* 65:55-63; Wilson, A. P., *Cytotoxicity and Viability Assays*. In: *Animal Cell Culture: A Practical Approach*, Vol. 1, pp. 175-219, 3rd ed. (Masters, J, ed.) Oxford University Press: Oxford, UK, 2000). This MTT assay is used widely to assess the cytotoxicity and selectivity of compounds such as anti-cancer drugs. The assay is suitable for rapid toxicity characterization of a test agent such as a drug formulation.

One way of assigning a cytotoxic activity to an agent is by converting the raw date to a $CD_{50}$ value, which represent the concentration of the agent needed to achieve 50% of the maximal cytotoxic activity. A lower $CD_{50}$ indicates a greater cytotoxic activity (as a lower amount of the agent is needed to achieve a fixed level of cytotoxicity). Two agents can be compared by examining the fold-increase or decrease in their $CD_{50}$ values.

The $CD_{50}$ values were interpolated from the curves generated using 12 serial dilutions. When individual compounds were used a single $CD_{50}$ value is shown. When a combination of two compounds was used, the $CD_{50}$ of both compounds is presented. The results of this study appear in Table 5, below. Values shown are the mean±standard error of three experiments with six readings per experiment.

TABLE 5

Cytotoxicity of VC, Hydroxytolan-1 and a VC/HT-1 combination against T24 Human Bladder Cancer Cells pretreated with a mixture of VC and VK$_3$

| Incubation Time | $CD_{50}$ (μM) of compounds tested Individually | | $CD_{50}$ (μM) of each compound tested in combination* after pretreatment with VC and VK$_3$** | |
|---|---|---|---|---|
| (days) | VC | HT-1 | VC | HT-1 |
| 1 | 849 ± 70.1 | 21.5 ± 7.4 | 226 ± 49 | 1.13 ± 0.25 |
| 2 | 896 ± 59.8 | 10.5 ± 2.7 | 187 ± 99 | 0.94 ± 0.55 |

*VC: HT-1 ratio in mixture was 200:1
**Cells were incubated with mixture of VC/VK3 at a ratio of 100:1 (150 μM VC and 1.5 μM VK$_3$ for 2 hrs before washing out this mixture and adding the VC/HT-1 mixture.

Ascorbate alone had a $CD_{50}$ of 849 μM. HT-1 alone had a $CD_{50}$ of 21.5 μM.

When the T24 cells were pretreated with 150 μM VC+1.5 μM VK$_3$ for 2 h and then exposed to a mixture of VC/HT-1 (ratio of 200:1), the $CD_{50}$ value of VC in the combination after 1 day decreased to 226 μM (i.e., the cytotoxic potency increased about 4-fold over VC alone) and the $CD_{50}$ value of the HT-1 decreased to 1.13 μM (i.e., the cytotoxic potency increased about 19-fold over HT-1 alone). After 2 days, the cytotoxic potency of the VC in the combination increased about 4.5-fold and the cytotoxic potency of HT-1 increased about 11-fold.

These results demonstrate that treating cancer cells with a combination of VC and VK3 sensitizes them to the cytotoxic action of HT-1 and renderings this compound surprisingly more active in its ability to kill cancer cells.

EXAMPLE 2

Effects of Combinations of a Hydroxytolan Compounds with VC and VK$_3$ In Vivo

A, Prostate Cancer:

A group of 30 men aged in their 70's suffering from prostate cancer receive a daily dosage of between 30 mg and 50 mg of compounds of formulas II, III or IV in combination with Vitamin C at a dose of 3 g and 5 g and VK$_3$ at a dose of 30 mg and 50 mg. Examination of the patients by clinical and histopathological tests shows significant shrinkage in tumors, and signs of cell death in 60% of the patients.

B, Bladder Cancer

A group of 20 men and 20 women aged 50-75 with bladder cancer are treated by intravenous injection of between 10 μg and 5 mg/kg of compounds of formulas II, III and IV in combination with Vitamin C at a dose of 1 g to 35 g weekly and VK$_3$ at a dose of 10 mg and 350 mg weekly over a period of three months. Clinical, radiographic and histopathological tests show significant remission in 40% of patients, accompanied by signs of cell death in 60%.

C. Breast Cancer

A group of 40 women with a past history of breast cancer who had been treated by surgery or radiation, or both, and women with a strong family history of breast cancer are treated as indicated below. This study test compounds of formulas II, III and IV administered transdermally each day through a skin patch for their action in preventing breast cancer or metastatic cancer following cancer therapy. Patches are prepared with a lipophilic carrier which is readily absorbed through the skin (glycerol cold cream containing glycerin and peanut oil). A selected active compound from any one of compounds of formulas II, III and IV is mixed with the lipophilic cream such that each patch comprises 10 mg to 100 mg of the active HT compound. The patch is applied to the skin each day, and rapid absorption occurs. After two hours, the patch is removed. Patients also receive a combination with Vitamin C at a dose of 1 g to 35 g weekly and VK$_3$ at a dose of 10 mg or 350 mg weekly over a period of up to 12 months.

Over a one-year study period, it is found that this high-risk group does not show any evidence of breast cancer or other metastatic cancer, therefore indicating the ability of these compounds to inhibit breast cancer development in high risk subjects.

In other studies, the same compounds and combinations successfully treat breast cancer

What is claimed is:

1. A method of treating a subject with prostate, bladder, colon or breast cancer, comprising administering to said subject in need thereof, a combination of compounds that comprises:

(a) an effective amount of one or more of a first compound selected from the group consisting of:

(i) hydroxytolan-1 (HT-1) or 4,4'-dihydroxytolan, the chemical structure of which is

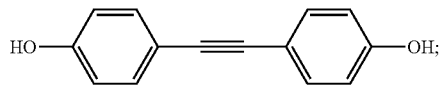

(ii) hydroxytolan-2 (HT-2) or 4-hydroxy-4'-trifluoromethyltolan, the chemical structure of which is

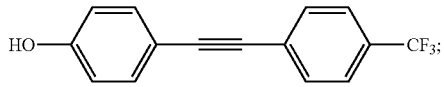

and (iii) hydroxytolan-3 (HT-3) or 3,4',5-trihydroxytolan or 3',4,5'-trihydroxytolan, the chemical structure of which is

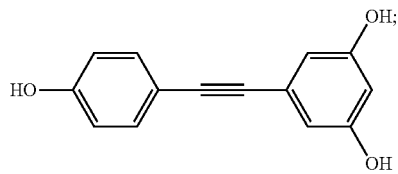 [SMILES: Oc1ccc(C#Cc2cc(O)cc(O)c2)cc1]

and (iv) hydroxytolan-4 (HT-4) or 3,3',5,5'-tetrahydroxytolan, the chemical structure of which is

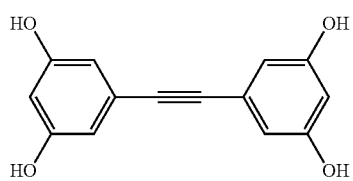 [SMILES: Oc1cc(O)cc(C#Cc2cc(O)cc(O)c2)c1]

and
(b) an amount of a second compound which is sodium ascorbate (VC) and a third compound which is Vitamin $K_3$ ($VK_3$) or an active quinone or semiquinone analogue of $VK_3$
wherein an anticancer effect of the combination of the first compound, the second compound and the third compound is statistically significantly greater than an anticancer effect of (i) said first compound alone or (ii) the combination of said second and said third compounds.

2. The method of claim 1 wherein the first compound is Hydroxytolan-1.

3. The method of claim 1 wherein the first compound is Hydroxytolan 2.

4. The method of claim 1 wherein the first compound is Hydroxytolan 3.

5. The method of claim 1 wherein the first compound is Hydroxytolan 4.

6. The method of claim 1, wherein the third compound is $VK_3$.

7. The method of claim 1, wherein the third compound is said quinone or semiquinone analogue of $VK_3$.

8. The method of claim 7 wherein the quinone is benzoquinone, naphthoquinone or anthraquinone.

9. The method of claim 1, wherein the first compound and the second compound are administered in a ratio of the VC to the first compound of between about 50 and about 900.

10. The method of claim 1, wherein the VC is administered orally to the subject at a daily dose of between about 15 mg and 1 g per kg body weight, and the amount of the third compound administered per day is between about 30 µg and about 20 mg per kg body weight.

11. The method of claim 1, wherein the presence of said $VK_3$ or said analogue increases the anticancer effect by at least about 20 percent over that produced by administration of the combination of the first compound and VC.

12. The method of claim 1, wherein the presence of said VC increases the anticancer effect by at least about 20 percent over that produced by administration of said combination of the first compound and the third compound.

13. The method of claim 1, wherein the cancer being treated is bladder cancer.

14. The method of claim 1 wherein said administering of the first compound, the second compound and the third compound is oral, intravenous or intraperitoneal.

15. The method of claim 1, wherein the cancer being treated is prostate cancer.

16. The method of claim 1, wherein the cancer being treated developed from a precancerous lesion.

17. The method of claim 1, wherein the cancer being treated is colon cancer.

18. The method of claim 1, wherein the cancer being treated is breast cancer.

19. A method of killing bladder, prostate, colon or breast cancer cells comprising administering to said subject in need thereof, a combination of compounds that comprises:
(a) an effective amount of one or more of a first compound selected from the group consisting of:

(i) hydroxytolan-1 (HT-1) or 4,4'-dihydroxytolan, the chemical structure of which is

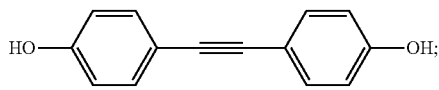 [SMILES: Oc1ccc(C#Cc2ccc(O)cc2)cc1]

(ii) hydroxytolan-2 (HT-2) or 4-hydroxy-4'-trifluoromethyltolan, the chemical structure of which is

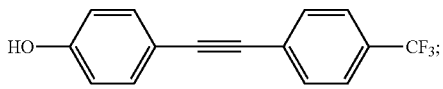

and
(iii) hydroxytolan-3 (HT-3) or 3,4',5-trihydroxytolan or 3',4,5'-trihydroxytolan, the chemical structure of which is

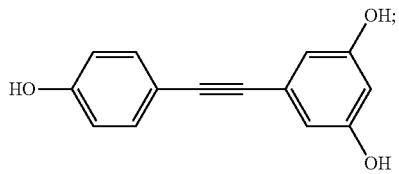

and
(iv) hydroxytolan-4 (HT-4) or 3,3',5,5'-tetrahydroxytolan, the chemical structure of which is

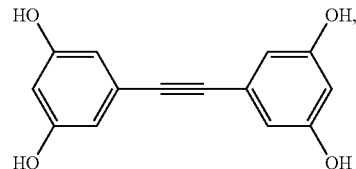 [SMILES: Oc1cc(O)cc(C#Cc2cc(O)cc(O)c2)c1]

and
(b) an amount of a second compound which is sodium ascorbate (VC) and a third compound which is Vitamin $K_3$ ($VK_3$) or an active quinone or semiquinone analogue of $VK_3$,
wherein the killing by the combination of the first compound, the second compound and the third compound is statistically significantly greater than the killing by (i) said first compound alone or (ii) the combination of said second and said third compounds.

20. The method of claim 19, wherein the presence of said $VK_3$ or said analogue increases the killing by at least about 20 percent over that produced by administration of the combination of the first compound and VC.

21. The method of claim 19, wherein the presence of said VC increases the killing by at least about 20 percent over that produced by administration of said combination of the first compound and the third compound.

22. The method of claim 19, wherein the cancer cells being killed are bladder cancer cells.

23. The method of claim 19, wherein the cancer cells being killed are prostate cancer cells.

24. The method of claim 19, wherein the cancer cells being killed are colon cancer cells.

25. The method of claim 19, wherein the cancer cells being killed are breast cancer cells.

26. The method of claim 19, wherein the cancer cells being killed are developed from a precancerous lesion.

* * * * *

UNITED STATES PATENT AND TRADEMARK OFFICE
CERTIFICATE OF CORRECTION

PATENT NO. : 8,680,142 B2  Page 1 of 1
APPLICATION NO. : 12/666080
DATED : March 25, 2014
INVENTOR(S) : Tsai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1016 days.

Signed and Sealed this

Twenty-ninth Day of September, 2015

Michelle K. Lee
*Director of the United States Patent and Trademark Office*